United States Patent
Nakamura et al.

(10) Patent No.: US 9,585,948 B2
(45) Date of Patent: Mar. 7, 2017

(54) TOMM34 PEPTIDES AND VACCINES INCLUDING THE SAME

(71) Applicant: ONCOTHERAPY SCIENCE, INC., Kanagawa (JP)

(72) Inventors: Yusuke Nakamura, Tokyo (JP); Takuya Tsunoda, Kanagawa (JP); Ryuji Osawa, Kanagawa (JP); Sachiko Yoshimura, Kanagawa (JP); Tomohisa Watanabe, Kanagawa (JP); Gaku Nakayama, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 14/810,287

(22) Filed: Jul. 27, 2015

(65) Prior Publication Data

US 2015/0374810 A1 Dec. 31, 2015

Related U.S. Application Data

(62) Division of application No. 13/990,766, filed as application No. PCT/JP2011/006551 on Nov. 25, 2011, now Pat. No. 9,125,849.

(60) Provisional application No. 61/419,181, filed on Dec. 2, 2010.

(51) Int. Cl.
| | |
|---|---|
| A61K 38/00 | (2006.01) |
| A61K 39/00 | (2006.01) |
| C07K 14/705 | (2006.01) |
| G01N 33/574 | (2006.01) |
| C07K 7/06 | (2006.01) |
| C12N 5/0783 | (2010.01) |

(52) U.S. Cl.
CPC ............ *A61K 39/0011* (2013.01); *C07K 7/06* (2013.01); *C07K 14/705* (2013.01); *C12N 5/0638* (2013.01); *G01N 33/57407* (2013.01); *A61K 38/00* (2013.01); *A61K 39/00* (2013.01); *A61K 2039/5154* (2013.01); *A61K 2039/5158* (2013.01); *A61K 2039/53* (2013.01); *C12N 2501/998* (2013.01); *C12N 2502/1114* (2013.01)

(58) Field of Classification Search
None
See application file for complete search history.

(56) References Cited

U.S. PATENT DOCUMENTS

| | | | |
|---|---|---|---|
| 5,539,084 | A | 7/1996 | Geysen et al. |
| 5,785,973 | A | 7/1998 | Bixler et al. |
| 5,840,839 | A | 11/1998 | Wang et al. |
| 7,514,084 | B2 | 4/2009 | Tahara et al. |
| 7,700,359 | B2 | 4/2010 | Chan et al. |
| 2004/0181344 | A1 | 9/2004 | Stephanopoulos et al. |
| 2004/0265230 | A1 | 12/2004 | Martinez et al. |
| 2008/0274129 | A1 | 11/2008 | Fikes et al. |
| 2009/0214571 | A1 | 8/2009 | Nakamura et al. |
| 2012/0093845 | A1 | 4/2012 | Tsunoda et al. |

FOREIGN PATENT DOCUMENTS

| | | |
|---|---|---|
| CN | 101278196 A | 10/2008 |
| JP | 2006-507802 A | 3/2006 |
| JP | 2009-502732 A | 1/2009 |
| JP | 2010-523471 A | 7/2010 |
| TW | 2008/44111 A | 11/2008 |
| WO | 01/49310 A1 | 7/2001 |
| WO | 03/104275 A2 | 12/2003 |
| WO | 2004/018667 A1 | 3/2004 |
| WO | 2004/024766 A1 | 3/2004 |
| WO | 2004/061423 A2 | 7/2004 |
| WO | 2007/013576 | * 2/2007 |
| WO | 2007/013576 A | 2/2007 |
| WO | 2007/013576 A1 | 2/2007 |
| WO | 2008/102557 A1 | 8/2008 |
| WO | 2008/126413 A1 | 10/2008 |
| WO | 2010/106770 A1 | 9/2010 |

OTHER PUBLICATIONS

Kent WO 2004/108753, Dec. 2004 (only pp. 1-98, drawings and ISR provided).*
Adams, et al., "Prediction of binding to MHC class I molecules " *J Immunol Methods*, vol. 185(2), pp. 181-190 (Sep. 25, 1995).
Belli, et al., "Vaccination of Metastatic Melanoma Patients With Autologous Tumor-Derived Heat Shock Protein gp96-Peptide Complexes: Clinical and Immunologic Findings," *J Clin. Oncol.*, vol. 20(20), pp. 4169-4180 (Oct. 15, 2002).
Boon, "Toward a Genetic Analysis of Tumor Rejection Antigens," *Adv Cancer Res.*, vol. 58, pp. 177-210 (1992).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.* vol. 183(3), pp. 725-729 (Mar. 1, 1996).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Celis, "Getting peptide vaccines to work: just a matter of quality control?", *J Clin Invest.*, vol. 110(12), pp. 1765-1768 (Dec. 2002).
Chaux, et al., "Estimation of the Frequencies of Anti-Mage-3 Cytolytic T-Lymphocyte Precursors in Blood From Individuals Without Cancer," *Int J Cancer.*, vol. 77(4), pp. 538-542 (Aug. 12, 1998).
Chen, et al., "Response of a Human T Cell Clone to a Large Panel of Altered Peptide Ligands Carrying Single Residue Substitutions in an Antigenic Peptide," *J Immunol.*, vol. 157(9), pp. 3783-3790 (Nov. 1, 1996).

(Continued)

*Primary Examiner* — Sheela J Huff
(74) *Attorney, Agent, or Firm* — Kilpatrick Townsend & Stockton LLP

(57) ABSTRACT

The present invention provides isolated peptides or the fragments derived from SEQ ID NO: 42, which bind to an HLA antigen and induce cytotoxic T lymphocytes (CTL). The peptides may include one of the above mentioned amino acid sequences with substitution, deletion, or addition of one, two, or several amino acids sequences. The present invention also provides pharmaceutical compositions including these peptides. The peptides of this invention can be used for treating cancer.

9 Claims, 2 Drawing Sheets

(56) References Cited

OTHER PUBLICATIONS

Chewawiwat, et al., "Characterization of the Novel Mitochondrial Protein Import component, Tom34, in Mammalian Cells," *J Biochem.*, vol. 125(4), pp. 721-727 (Apr. 1999).
Coulie, et al, "Cytolytic T-cell responses of caner patients vaccinated with a MAGE antigen," *Immunol Rev.*, vol. 188, pp. 33-42 (Oct. 2002).
Dionne, et al., "Functional characterization of CTL against gp100 altered peptide ligands," *Cancer Immunol Immunother.*, vol. 53(4), pp. 199-206 (Apr. 2003, Epub Feb. 18, 2003).
Dionne, et al., "Her-2/*neu* altered peptide ligand-induced interaction CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Evans, et al., "Vaccine therapy for cancer—fact or fiction?", *QJ Med.*, vol. 92(6), pp. 299-307 (Jun. 1999).
Falk, et al., "Allele-specific motifs revealed by sequencing of self-peptide eluted from MHC molecules," *Nature*, vol. 351(6324), pp. 290-296 (May 23, 1991).
Fujie, et al., "A *Mage*-1 Encoded HLA-A-A24-Binding Synthetic Peptide Induces Specific Anti-Tumor Cytotoxic T Lymphocytes," *Int J Cancer*, vol. 80(2), pp. 169-172 (Jan. 18, 1999).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Hazama, et al., "Novel Vaccine Strategies for Colorectal Cancer," *Biotherapy*, vol. 23(2), pp. 160-164 (2009).
Hoffmann, et al., "The Ability of Variant Peptides to Reverse the Nonresponsiveness of T Lymphocytes to the Wild-Type Sequence p53$_{264-272}$ Epitope," *J Immunol.*, vol. 168(3), pp. 1338-1347 (Feb. 1, 2002).
Ida, et al., "Crisscross CTL Induction by SYT-SSX Junction Peptide and Its HLA-A 2402 Anchor Substitute," *J Immunol.*, vol. 173(2), pp. 1436-1443 (Jul. 15, 2004).
Kalejs, et al., "Cancer/testis antigens and gametogenesis: a review and "brain-storming" session", *Cancer Cell Int.*, vol. 5(1):4, 11 pages (Feb. 16, 2005).
Kikuchi, et al., "Identification of a SART-1-Dervied Peptide Capable of Inducing HLA-A24-Restricted and Tumor-Specific Cytotoxic T Lymphocytes," *Int J Cancer*, vol. 81(3), pp. 459-466 (May 5, 1999).
Kirkin, et al., "Melanoma-associated antigens recognized by cutotoxic T lymphocytes," *APMIS*, vol. 106(7), pp. 665-679 (Jul. 1998).
Kondo, et al., "Prominent Roles of Secondary Anchor Residues in Peptide Binding to HLA-A24 Human Class I Molecules," *J. Immunol.*, vol. 155(9), pp. 4307-4312 (Nov. 1, 1995).
Kubo, et al., "Definition of Specific Peptide Motifs for Four Major HLA-A Alleles," *J Immunol.*, vol. 152(8), pp. 3913-3924 (Apr. 15, 1994).
Lee, et al., "Increased Vaccine-Specific T Cell Frequency After Peptide-Based Vaccination Correlates with Increased Susceptibility to In Vitro Stimulation But Does Not Lead to Tumor Regression," *J Immunol.*, vol. 163(11), pp. 6292-6300 (Dec. 1, 1999).
Mukhopadhyay, et al., "Tom34 Unlike Tom20 Does Not Interact with the Leader Sequences of Mitochondrial Precursor Proteins," *Arch Biochem Biophys.*, vol. 400(1), pp. 97-104 (Apr. 1, 2002).

Nuttall, et al., "hTom34: A Novel Translocase for the Import of Proteins into Human Mitochondria," *DNA Cell Biol.*, vol. 16(9), pp. 1067-1074 (Sep. 1997).
Oiso, et al., "A Newly Identified *Mage*-3-Derived Epitope Recognized by HLA-A24-Restricted Cytotoxic T Lymphocytes," *Int J Cancer*, vol. 81(3), pp. 387-394 (May 5, 1999).
Okuno, et al., "Phase I clinical trial of a novel peptide vaccine in combination with UFT/LV for metastatic colorectal cancer," *Exp Ther Med.*, vol. 2(1), pp. 736-79 (Jan. 2011, Epub Dec. 2, 2010).
Parker, et al., "Scheme for Ranking Potential HLA-A2 Binding Peptides Based in Independent Binding of Individual Peptide Side-Chains," *J Immunol.*, vol. 152(1), pp. 163-175 (Jan. 1, 1994).
Rammensee, et al., "MHC ligands and peptide motifs: first listing," *Immunogenetics*, vol. 41(4), pp. 178-228 (1995).
Roitt, et al., *Immunology*, 4th ed., 7.9-7.11, 3 pages (1996).
Rosenberg, et al., "Cancer immunotherapy: moving beyond current vaccines," *Nat Med.*, vol. 10(9), pp. 909-915 (Sep. 2004).
Schueler-Furman, et al., "Structure-based prediction of binding peptides to MHC class I molecules: Application to a broad range of MHC alleles," *Protein Sci.*, vol. 9(9), pp, 1838-1846 (Sep. 2000).
Shimokawa, et al., "Identification of TOMM34, which shows elevated expression in the majority of human colon cancers, as a novel drug target," *Int J Oncol.*, vol. 29(2), pp. 381-386 (Aug. 2006).
Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).
Terada, et al., "Expression of Tom23 Splicing Isoforms in Mouse Testis and Knock-out of *Tom34* in Mice," *J Biochem.*, vol. 133(5), pp. 625-631 (May 2003).
Van Der Burg, et al., "Immunogenicity of Peptides Molecules Depends on the MHC Class I Molecules Depends on the MHC-Peptide Complex Stability," *J Immunol.*, vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).
Yang, et al., "Yeast Two-Hybrid Screening Identifies Binding Partners of Human Tom34 That Have ATPase Activity and Form a Complex With Tom34 in the Cytosol," *Arch Biochem Biophys.*, vol. 400(1), pp. 105-100 (Apr. 1, 2002).
Zaremba, et al., "Identification of an EnhancerAgonist Cytotoxic T Lymphocyte Peptide from Human Carcinoembryonic Antigen," *Cancer Res.*, vol. 57(20), pp. 4570-4577 (Oct. 15, 1997).
International Search Report and Written Opinion for PCT/JP2011/006551, 15 pages, mailed Dec. 20, 2011.
Stevanovic, "Identification of Tumour-Associated T-Cell Epitopes for Vaccine Development", *Nat Rev Cancer*, 2(7):514-520 (2002).
Engelhard, "Structure of peptides associated with MHC Class I Molecules", *Current Opinion in Immunology*, vol. 6, No. 1, pp. 13-23 (1994).
Shastri et al., "Presentation of Endogenous Peptide/MHC Class I Complexes is Profoundly Influenced by Specific C-Terminal Flanking Residues",*J. Immunol.*, vol. 155, No. 9, pp. 4339-4346 (1995).
Guo et al., "Different length peptides bind to HLA-Aw68 similarly at their ends but bulge out in the middle". *Nature*, vol. 360., pp. 364-366 (1992).

* cited by examiner

```
                        SEQUENCE LISTING

<160> NUMBER OF SEQ ID NOS: 46

<210> SEQ ID NO 1
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 1

Ala Leu Tyr Gly Arg Ala Leu Arg Val
1               5

<210> SEQ ID NO 2
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 2

Ala Leu Ala Leu Val Pro Phe Ser Ile
1               5

<210> SEQ ID NO 3
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 3

Val Leu Tyr Ser Asn Arg Ala Ala Cys
1               5

<210> SEQ ID NO 4
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 4

Thr Val Leu Gln Ile Asp Asp Asn Val
1               5

<210> SEQ ID NO 5
<211> LENGTH: 9
<212> TYPE: PRT
<213> ORGANISM: Artificial Sequence
<220> FEATURE:
<223> OTHER INFORMATION: an artificially synthesized peptide sequence
```

```
<400> SEQUENCE: 5

Leu Leu Cys Ser Asn Leu Glu Ser Ala
1               5

<210> SEQ ID NO 6
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 6

Tyr Ser Asn Arg Ala Leu Cys Tyr Leu
1               5

<210> SEQ ID NO 7
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 7

Met Ala Tyr Val Asp Tyr Lys Thr Val
1               5

<210> SEQ ID NO 8
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 8

Leu Val Pro Phe Ser Ile Lys Pro Leu
1               5

<210> SEQ ID NO 9
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 9

Lys Leu Asp Gly Lys Asn Val Lys Ala
1               5

<210> SEQ ID NO 10
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 10

Gly Gln Tyr Ala Glu Ala Ser Ala Leu
1               5

<210> SEQ ID NO 11
<211> LENGTH: 9
<212> TYPE: PRT
<213> ORGANISM: Artificial Sequence
<220> FEATURE:
<223> OTHER INFORMATION: an artificially synthesized peptide sequence
```

```
<400> SEQUENCE: 11

Val Leu Lys Glu Glu Gly Asn Glu Leu
1               5

<210> SEQ ID NO 12
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 12

Val Leu Gln Ile Asp Asp Asn Val Thr
1               5

<210> SEQ ID NO 13
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 13

Leu Val Leu Lys Gln Tyr Thr Glu Ala
1               5

<210> SEQ ID NO 14
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 14

Met Ala Pro Lys Phe Pro Asp Ser Val
1               5

<210> SEQ ID NO 15
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 15

Gln Ile Asp Asp Asn Val Thr Ser Ala
1               5

<210> SEQ ID NO 16
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 16

Ala Leu Lys Leu Asp Gly Lys Asn Val
1               5

<210> SEQ ID NO 17
<211> LENGTH: 9
<212> TYPE: PRT
<213> ORGANISM: Artificial Sequence
<220> FEATURE:
<223> OTHER INFORMATION: an artificially synthesized peptide sequence
```

```
<400> SEQUENCE: 17

Val Leu Lys Gln Tyr Thr Glu Ala Val
1               5

<210> SEQ ID NO 18
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 18

Leu Pro Ser Ile Pro Leu Val Pro Val
1               5

<210> SEQ ID NO 19
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 19

Leu Lys Leu Pro Ser Ile Pro Leu Val
1               5

<210> SEQ ID NO 20
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 20

Ser Ser Phe Ala Asp Ile Ser Asn Leu
1               5

<210> SEQ ID NO 21
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 21

Lys Leu Pro Ser Ile Pro Leu Val Pro Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 22

Ala Leu Glu Lys Tyr Pro Met Ala Tyr Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: an artificially synthesized peptide sequence
```

```
<400> SEQUENCE: 23

Ala Leu Val Pro Phe Ser Ile Lys Pro Leu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 24

Tyr Leu Val Leu Lys Gln Tyr Thr Glu Ala
1               5                   10

<210> SEQ ID NO 25
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 25

Ser Leu Gly Pro Glu Trp Arg Leu Lys Leu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 26

Ser Leu Leu Cys Ser Asn Leu Glu Ser Ala
1               5                   10

<210> SEQ ID NO 27
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 27

Leu Val Leu Lys Gln Tyr Thr Glu Ala Val
1               5                   10

<210> SEQ ID NO 28
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 28

Arg Met Thr Arg Ala Leu Met Asp Ser Leu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: an artificially synthesized peptide sequence
```

```
<400> SEQUENCE: 29

Gln Ile Asp Asp Asn Val Thr Ser Ala Val
1               5                   10

<210> SEQ ID NO 30
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 30

Lys Gln Tyr Thr Glu Ala Val Lys Asp Cys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 31

Ala Leu Tyr Gly Arg Ala Leu Arg Val Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 32

Leu Leu Cys Ser Asn Leu Glu Ser Ala Thr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 33

Val Leu Lys Glu Glu Gly Asn Glu Leu Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 34

Leu Gln Ile Asp Asp Asn Val Thr Ser Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: an artificially synthesized peptide sequence
```

```
<400> SEQUENCE: 35

Arg Val Leu Lys Glu Glu Gly Asn Glu Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 36

Lys Leu Arg Gln Glu Val Lys Gln Asn Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 37

Arg Leu Lys Leu Pro Ser Ile Pro Leu Val
1               5                   10

<210> SEQ ID NO 38
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 38

Ser Leu Pro Ser Glu Asn His Lys Glu Met
1               5                   10

<210> SEQ ID NO 39
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 39

Lys Glu Thr Thr Ala Thr Lys Asn Arg Val
1               5                   10

<210> SEQ ID NO 40
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 40

Ser Ala Gly Asp Val Glu Lys Ala Arg Val
1               5                   10

<210> SEQ ID NO 41
<211> LENGTH: 2066
<212> TYPE: DNA
<213> ORGANISM: Homo sapiens
```

<400> SEQUENCE: 41

```
aggtctcgca ggccccgccc cctcgccgcg ggttcgctgt tgggcggaga tattcgccgc      60
cggcgcttgc gcccggaagg tgtgccgcac cacacggggg aggaaggaag gagctcccaa     120
ctcgccggcc tggccacggg atggccccca aattcccaga ctctgtggag gagctccgcg     180
ccgccggcaa tgagagtttc cgcaacggcc agtacgccga ggcctccgcg ctctacggcc     240
gcgcgctgcg ggtgctgcag gcgcaaggtt cttcagaccc agaagaagaa agtgttctct     300
actccaaccg agcagcatgt cacttgaagg atggaaactg cagagactgc atcaaagatt     360
gcacttcagc actggccttg gttcccttca gcattaagcc cctgctgcgg cgagcatctg     420
cttatgaggc tctggagaag taccctatgg cctatgttga ctataagact gtgctgcaga     480
ttgatgataa tgtgacgtca gccgtagaag gcatcaacag aatgaccaga gctctcatgg     540
actcgcttgg gcctgagtgg cgcctgaagc tgccctcaat ccccttggtg cctgtttcag     600
ctcagaagag gtggaattcc ttgccttcgg agaaccacaa agagatggct aaaagcaaat     660
ccaaagaaac cacagctaca aagaacagag tgccttctgc tggggatgtg agaaagccca     720
gagttctgaa ggaagaaggc aatgagcttg taaagaaggg aaaccataag aaagctattg     780
agaagtacag tgaaagcctc ttgtgtagta acctggaatc tgccacgtac agcaacagag     840
cactctgcta tttggtcctg aagcagtaca cagaagcagt gaaggactgc acagaagccc     900
tcaagctgga tggaaagaac gtgaaggcat tctacagacg ggctcaagcc cacaaagcac     960
tcaaggacta taaatccagc tttgcagaca tcagcaacct cctacagatt gagcctagga    1020
atggtcctgc acagaagttg cggcaggaag tgaagcagaa cctacactaa aacccaaca    1080
gggcaactgg aaccctgcc tgaccttacc cagagaagcc atgggccacc tgctctgtgc    1140
ccgctcctga aacccagcat gccccaagtg agctctgaag cccctcctc aatcccttga    1200
tggcctccca ccctgtaaga ggctttgctt gttcaaatta aactcagtgt agtcaaacac    1260
agacatggtt gttgcaccag aaaggtcccc actagagcta agcgtgaagc tgaagctctg    1320
tccctattcc cccagcccag ctagctgatc acaccaacag atcctcatca gcaaagcatt    1380
tggctttgtc ctgcccaagt gggctgcaga ctgagtgctg cccttgtagc ttccccagac    1440
cccaactcac tgcagttcat ctgaacaacc tgagctcctg ggccggggtg aaggaggggg    1500
gataaaccta aggccctgat ccaaagcagc ctgttgagct ggttctccag ggctgcagtc    1560
tctccaggtg tacagctgct gtccctgccc tgtcctgtcc ttgcacagtc tcctatgtct    1620
gagccccagt gccttctgtt cgggccctcc tttggtggga aggcagagcc ctgacccttg    1680
aatggttgtc cttgactctg tgctgctgcc ttctgcagag aggcacctaa gctgtttaaa    1740
gagcccagtg attgtggctg ctcctcctag aggtgggagg gggcaagagg cctccttggt    1800
cagtgtccat gctttctggg cagggacttg gttttttgtt ccaacagtgg ccttctccgg    1860
gcttcatagt tctttgtaat atgttgaagt taatttgaat tgactgattt tgttgaactg    1920
tgtgtttaag ctgttgcatt aaaaagcttt cttctacatc aatatctgct gtgctttcat    1980
ttatgccttt tcagctttgc acctggaact ctgtagtaat aataaaagtt attgcttatt    2040
gggcattcaa aaaaaaaaa aaaaaa                                          2066
```

<210> SEQ ID NO 42
<211> LENGTH: 309
<212> TYPE: PRT
<213> ORGANISM: Homo sapiens

```
<400> SEQUENCE: 42

Met Ala Pro Lys Phe Pro Asp Ser Val Glu Glu Leu Arg Ala Ala Gly
1               5                   10                  15

Asn Glu Ser Phe Arg Asn Gly Gln Tyr Ala Glu Ala Ser Ala Leu Tyr
            20                  25                  30

Gly Arg Ala Leu Arg Val Leu Gln Ala Gln Gly Ser Ser Asp Pro Glu
        35                  40                  45

Glu Glu Ser Val Leu Tyr Ser Asn Arg Ala Ala Cys His Leu Lys Asp
    50                  55                  60

Gly Asn Cys Arg Asp Cys Ile Lys Asp Cys Thr Ser Ala Leu Ala Leu
65                  70                  75                  80

Val Pro Phe Ser Ile Lys Pro Leu Leu Arg Arg Ala Ser Ala Tyr Glu
                85                  90                  95

Ala Leu Glu Lys Tyr Pro Met Ala Tyr Val Asp Tyr Lys Thr Val Leu
            100                 105                 110

Gln Ile Asp Asp Asn Val Thr Ser Ala Val Glu Gly Ile Asn Arg Met
        115                 120                 125

Thr Arg Ala Leu Met Asp Ser Leu Gly Pro Glu Trp Arg Leu Lys Leu
    130                 135                 140

Pro Ser Ile Pro Leu Val Pro Val Ser Ala Gln Lys Arg Trp Asn Ser
145                 150                 155                 160

Leu Pro Ser Glu Asn His Lys Glu Met Ala Lys Ser Lys Ser Lys Glu
                165                 170                 175

Thr Thr Ala Thr Lys Asn Arg Val Pro Ser Ala Gly Asp Val Glu Lys
            180                 185                 190

Ala Arg Val Leu Lys Glu Gly Asn Glu Leu Val Lys Lys Gly Asn
        195                 200                 205

His Lys Lys Ala Ile Glu Lys Tyr Ser Glu Ser Leu Leu Cys Ser Asn
    210                 215                 220

Leu Glu Ser Ala Thr Tyr Ser Asn Arg Ala Leu Cys Tyr Leu Val Leu
225                 230                 235                 240

Lys Gln Tyr Thr Glu Ala Val Lys Asp Cys Thr Glu Ala Leu Lys Leu
                245                 250                 255

Asp Gly Lys Asn Val Lys Ala Phe Tyr Arg Arg Ala Gln Ala His Lys
            260                 265                 270

Ala Leu Lys Asp Tyr Lys Ser Ser Phe Ala Asp Ile Ser Asn Leu Leu
        275                 280                 285

Gln Ile Glu Pro Arg Asn Gly Pro Ala Gln Lys Leu Arg Gln Glu Val
    290                 295                 300

Lys Gln Asn Leu His
305

<210> SEQ ID NO 43
<211> LENGTH: 22
<212> TYPE: DNA
<213> ORGANISM: Artificial Sequence
<220> FEATURE:
<223> OTHER INFORMATION: A synthesized 5' primer sequence for TCR

<400> SEQUENCE: 43
gtctaccagg cattcgcttc at                                          22

<210> SEQ ID NO 44
<211> LENGTH: 24
<212> TYPE: DNA
<213> ORGANISM: Artificial Sequence
```

```
<220> FEATURE:
<223> OTHER INFORMATION: A synthesized 3' primer sequence for TCR alpha
      C region

<400> SEQUENCE: 44
tcagctggac cacagccgca gcgt                                              24

<210> SEQ ID NO 45
<211> LENGTH: 21
<212> TYPE: DNA
<213> ORGANISM: Artificial Sequence
<220> FEATURE:
<223> OTHER INFORMATION: A synthesized 3' primer sequence for TCR beta
      C1 region

<400> SEQUENCE: 45
tcagaaatcc tttctcttga c                                                 21

<210> SEQ ID NO 46
<211> LENGTH: 24
<212> TYPE: DNA
<213> ORGANISM: Artificial Sequence
<220> FEATURE:
<223> OTHER INFORMATION: A synthesized 3' primer sequence for TCR beta
      C2 region

<400> SEQUENCE: 46
ctagcctctg gaatcctttc tctt                                              24
```

TOMM34 PEPTIDES AND VACCINES INCLUDING THE SAME

PRIORITY

The present application claims the benefit of U.S. Provisional Application No. 61/419,181 filed on Dec. 2, 2010, the entire contents of which are incorporated by reference herein.

TECHNICAL FIELD

The present invention relates to the field of biological science, more specifically to the field of cancer therapy. In particular, the present invention relates to novel peptides that are extremely effective as cancer vaccines, and drugs for treating and preventing tumors.

BACKGROUND ART

It has been demonstrated that CD8-positive CTLs recognize epitope peptides derived from tumor-associated antigens (TAAs) on the major histocompatibility complex (MHC) class I molecule, and then kill the tumor cells. Since the discovery of melanoma antigen (MAGE) family as the first example of TAAs, many other TAAs have been discovered through immunological approaches (NPLs 1, 2), and some of these TAAs are now in the process of clinical development as immunotherapeutic targets.

Favorable TAA is indispensable for proliferation and survival of cancer cells, as a target for immunotherapy, because the use of such TAAs may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses warrants further development and thus clinical application of peptide vaccination strategies for various types of cancer is ongoing (NPLs 3 to 10). To date, several clinical trials using these TAA derived peptides have been reported. Unfortunately, many of the current cancer vaccine trials have shown only a low objective response rate (NPLs 11 to 13). Accordingly, there remains a need for new TAAs as immunotherapeutic targets.

The TOMM34 gene (GenBank Accession No. NM_006809), translocase of outer mitochondrial membrane 34, has been identified from human EST and cDNA databases and predicted to encode a protein containing degenerated tetratricopeptide repeat (TPR) motifs (NPL 14). The protein encoded by this gene is involved in the import of precursor proteins into mitochondria. This protein has a chaperone-like activity, binding the mature portion of unfolded proteins and aiding their import into mitochondria (NPL 15).

In a recent study, it was indicated that TOMM34 is frequently up-regulated in colorectal cancer by gene-expression profile analysis using cDNA microarray consisting of 23040 genes. Furthermore, knockdown of TOMM34 by siRNA in colon cancer cell lines attenuated the growth of colon cancer cells (NPL 16).

CITATION LIST

Patent Literature

[PTL 1] PCT/JP2006/314947

Non Patent Literature

[NPL 1] Boon T, Int J Cancer 1993, 54(2): 177-80
[NPL 2] Boon T & van der Bruggen P, J Exp Med 1996, 183(3): 725-9
[NPL 3] Harris C C, J Natl Cancer Inst 1996, 88(20): 1442-55
[NPL 4] Butterfield L H et al., Cancer Res 1999, 59(13): 3134-42
[NPL 5] Vissers J L et al., Cancer Res 1999, 59(21): 5554-9
[NPL 6] van der Burg S H et al., J Immunol 1996, 156(9): 3308-14
[NPL 7] Tanaka F et al., Cancer Res 1997, 57(20): 4465-8
[NPL 8] Fujie T et al., Int J Cancer 1999, 80(2): 169-72
[NPL 9] Kikuchi M et al., Int J Cancer 1999, 81(3): 459-66
[NPL 10] Oiso M et al., Int J Cancer 1999, 81(3): 387-94
[NPL 11] Belli F et al., J Clin Oncol 2002, 20(20): 4169-80
[NPL 12] Coulie P G et al., Immunol Rev 2002, 188: 33-42
[NPL 13] Rosenberg S A et al., Nat Med 2004, 10(9): 909-15
[NPL 14] Nuttal S D et al., DNA Cell Biol. 1997 September; 16(9):1067-74
[NPL 15] Mukhopadhyay A et al., Arch Biochem Biophys. 2002 Apr. 1; 400(1):97-104
[NPL 16] Shimokawa et al., Int J Oncol. 2006 August; 29(2):381-6

SUMMARY OF INVENTION

The present invention is based, at least in part, on the discovery of novel peptides that may serve as suitable targets of immunotherapy. Because TAAs are generally perceived by the immune system as "self" and therefore often have no immunogenicity, the discovery of appropriate targets is of extreme importance. As noted above, TOMM34 (for example, SEQ ID NOs: 41 and 42, also indicated in GenBank Accession No. NM_006809) has been identified as up-regulated in cancers, including, but are not limited to, acute myelogenous leukemia (AML), chronic myelogenous leukemia (CML), bladder cancer, breast cancer, cervical cancer, colorectal cancer, esophagus cancer, liver cancer, osteosarcoma, prostate cancer, renal carcinoma, small cell lung cancer (SCLC), non-small cell lung cancer (NSCLC) and soft tissue tumor. Thus, the present invention focuses on TOMM34 as an appropriate cancer marker and a candidate for the target of immunotherapy.

In the course of the present invention, specific epitope peptides of the gene products of TOMM34 that possess the ability to induce CTLs specific to TOMM34 were identified. As discussed in greater detail below, peripheral blood mononuclear cells (PBMCs) obtained from a healthy donor were stimulated using HLA-A*0201 binding candidate peptides derived from TOMM34. CTL lines were then established with specific cytotoxicity against the HLA-A2 positive target cells pulsed with each of candidate peptides. The results herein demonstrate that these peptides are HLA-A2 restricted epitope peptides that may induce potent and specific immune responses against cells expressing TOMM34. These results further indicate that TOMM34 is strongly immunogenic and the epitopes thereof are effective targets for tumor immunotherapy.

Accordingly, it is an object of the present invention to provide isolated peptides that bind to HLA antigen and include the amino acid sequence of TOMM34 (SEQ ID NO: 42) or the immunologically active fragments thereof. These peptides are expected to have CTL inducibility and, thus, can be used to induce CTL in vitro or ex vivo, or to be administered to a subject for inducing immune responses against cancers, examples of which include, but are not limited to AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor. Preferred those peptides are nonapeptides or decapeptides, and, more preferably, a nonapeptide or decapeptide consisting of an amino acid sequence selected from among SEQ ID NOs: 1 to 20 and 22 to 40. Of these, the peptides having an amino acid sequence selected from among SEQ TD NOs: 1, 5, 31 and 32 showed particularly strong CTL inducibility and thus are particularly preferred.

The present invention also contemplates modified peptides having an amino acid sequence of an immunologically active fragment of TOMM34 in which one, two or more amino acids are substituted, deleted, inserted or added, so long as the modified peptides retain the requisite CTL inducibility of the original unmodified peptide. Of these, peptide having an amino sequence of SEQ ID NO: 1, 5, 31 or 32 in which one, two or more amino acids are substituted, deleted, inserted or added are particularly preferred.

The present invention further encompasses isolated polynucleotides encoding any peptides of the present invention. These polynucleotides can be used to induce or prepare APCs having CTL inducibility. Like the above-described peptides of the present invention, such APCs can be administered to a subject for inducing immune responses against cancers.

When administered to a subject, the present peptides are presented on the surface of APCs so as to induce CTLs targeting the respective peptides. Therefore, one object of the present invention is to provide compositions or agents including any peptides or polynucleotides provided by the present invention for inducing CTL. Such compositions or agents, including any peptides or polynucleotides, can be used for the treatment and/or prophylaxis of cancers or the prevention of a postoperative recurrence of cancer, examples of which include, but are not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor, and/or preventing postoperative recurrence thereof.

The present invention also contemplates pharmaceutical agents or compositions that include or incorporate one or more peptides or polynucleotides of the present invention formulated for the treatment and/or prophylaxis of cancer, particularly a primary cancer, or the prevention of a postoperative recurrence thereof. Instead of or in addition to the present peptides or polynucleotides, the present pharmaceutical agents or compositions may include as active ingredients APCs or exosomes that present any of the present peptides.

The peptides or polynucleotides of the present invention may be used to induce APCs which present on their surface a complex of an HLA antigen and the present peptide, for example, by contacting APCs derived from a subject with the peptide or introducing a polynucleotide encoding a peptide of this invention into APCs. Such APCs have high CTL inducibility against target peptides and are useful for cancer immunotherapy. Accordingly, the present invention contemplates both methods for inducing APCs with CTL inducibility and the APCs obtained by such methods.

It is a further object of the present invention to provide methods for inducing CTLs, such methods including the step of co-culturing CD8-positive cells with APCs or exosomes presenting the peptide of the present invention on its surface or the step introducing a polynucleotide/polynucleotides encoding T cell receptor (TCR) subunit polypeptides, wherein the TCR formed by such subunit polypeptides is capable of binding to a complex of an HLA antigen and the present peptide on a cell surface. CTLs obtained by such methods are useful in the treatment and prevention of cancers, examples of which include, but are not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

Yet another object of the present invention is to provide isolated APCs that present on the surface a complex of an HLA antigen and a peptide of the present invention. The present invention further provides isolated CTLs that target peptides of the present invention. These APCs and CTLs may be used for cancer immunotherapy.

It is yet another object of the present invention to provide methods for inducing an immune response against a cancer in a subject in need thereof, such methods including the step of administering to the subject a composition or agent that include one or more peptides of the present invention, polynucleotides encoding the peptide of the present invention, or exosomes or APCs presenting the peptide of the present invention.

The applicability of the present invention extends to any of a number of diseases relating to or arising from TOMM34 overexpression, such as cancer, exemplary cancers including, but not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

More specifically, the present invention provides the following [1] to [20]:

[1] An isolated peptide following (a) or (b):
  (a) an isolated peptide comprising an amino acid sequence selected from the group consisting of SEQ ID NOs: 1, 5 31 and 32;
  (b) an isolated peptide comprising an amino acid sequence in which one, two, or several amino acid(s) are substituted, deleted, inserted or added to an amino acid sequence selected from the group consisting of SEQ ID NOs: 1, 5, 31 and 32 to yield a modified peptide that retains the ability to bind to an HLA antigen and cytotoxic T lymphocyte (CTL) inducibility;

[2] The isolated peptide of [1], wherein the HLA antigen is HLA-A2;

[3] The isolated peptide of [1] or [2], wherein said peptide is a nonapeptide or decapeptide;

[4] The peptide of any one of [1] to [3], having at least one substitution selected from the group consisting of:
  (a) the second amino acid from N-terminus is or is modified to be an amino acid selected from the group consisting of leucine and methionine, and
  (b) the C-terminal amino acid is or is modified to be an amino acid selected from the group consisting of valine and leucine;

[5] An isolated polynucleotide encoding the peptide of any one of [1] to [4];

[6] A composition for inducing CTL, wherein the composition comprises one or more peptide(s) of any one of [1] to [4], or one or more polynucleotide(s) of [5];

[7] A pharmaceutical composition comprising:
  (a) one or more peptide(s) of any one of [1] to [4];
  (b) one or more polynucleotides of [5];
  (c) one or more APCs or exosomes that present a complex of the peptide of any one of [1] to [4] and an HLA antigen on their surface; or (d) one or more CTLs that recognize a cell presenting a complex of the peptide of any one of [1] to [4] and an HLA antigen on its surface,
in combination with pharmaceutically acceptable carrier, formulated for a purpose selected from the group consisting of:
(i) treatment of an existing cancer,
(ii) prophylaxis of a cancer,
(iii) prevention of a postoperative recurrence of a cancer, and
(vi) combinations thereof;

[8] The pharmaceutical composition of [7] formulated for administration to a subject whose HLA antigen is HLA-A2;

[9] A method for inducing an antigen-presenting cell (APC) with CTL inducibility, comprising a step selected from the group consisting of:
(a) contacting an APC with the peptide of any one of [1] to [4] in vitro, ex vivo or in vivo, and
(b) introducing a polynucleotide encoding the peptide of any one of [1] to [4] into an APC.

[10] A method for inducing a CTL, comprising a step selected from the group consisting of:
(a) co-culturing a CD8-positive T cell with an APC that presents on its surface a complex of an HLA antigen and the peptide of any one of [1] to [4],
(b) co-culturing a CD8-positive T cell with an exosome that presents on its surface a complex of an HLA antigen and a peptide of any one of [1] to [4], and
(c) introducing into a T cell a polynucleotide/polynucleotides encoding T cell receptor (TCR) subunit polypeptides, wherein the TCR formed by said TCR subunit polypeptides is capable of binding to a complex of an HLA antigen and the peptide of any one of [1] to [4] on a cell surface;

[11] An isolated APC that presents on its surface a complex of an HLA antigen and a peptide of any one of [1] to [4];

[12] The APC of [11], which is induced by a method for inducing an antigen-presenting cell (APC) with CTL inducibility, wherein the method comprises a step selected from the group consisting of:
(a) contacting an APC with the peptide of any one of [1] to [4] in vitro, ex vivo or in vivo, and
(b) introducing a polynucleotide encoding the peptide of any one of [1] to [4] into an APC;

[13] An isolated CTL that targets any of the peptides of [1] to [4];

[14] The CTL of [13], which is induced by a method for inducing a CTL, wherein the method comprises a step selected from the group consisting of:
(a) co-culturing a CD8-positive T cell with an APC that presents on its surface a complex of an HLA antigen and the peptide of any one of [1] to [4],
(b) co-culturing a CD8-positive T cell with an exosome that presents on its surface a complex of an HLA antigen and a peptide of any one of [1] to [4], and
(c) introducing into a T cell a polynucleotide/polynucleotides encoding T cell receptor (TCR) subunit polypeptides, wherein the TCR formed by said TCR subunit polypeptides is capable of binding to a complex of an HLA antigen and the peptide of any one of [1] to [4] on a cell surface;

[15] A method of inducing an immune response against cancer in a subject, comprising the step of administering to the subject a peptide of [1] to [4], an immunologically active fragment thereof, or a polynucleotide encoding the peptide or the fragment;

[16] A vector comprising a nucleotide sequence encoding the peptide of any one of [1] to [4];

[17] A host cell transformed or transfected with an expression vector of [16];

[18] An exosome that presents a complex comprising the peptide of any one of [1] to [4] and an HLA antigen;

[19] An antibody against the peptide of any one of [1] to [4], or immunologically active fragment thereof; and

[20] A diagnostic kit comprising the peptide of any one of [1] to [4], the polynucleotide of [5] or antibody or immunologically active fragment of [19].

Objects and features of the invention will become more fully apparent when the following detailed description is read in conjunction with the accompanying figures and examples. It is to be understood that both the foregoing summary of the present invention and the following detailed description are of exemplified embodiments, and not restrictive of the present invention or other alternate embodiments of the present invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follows.

DESCRIPTION OF EMBODIMENTS

Figure 1:
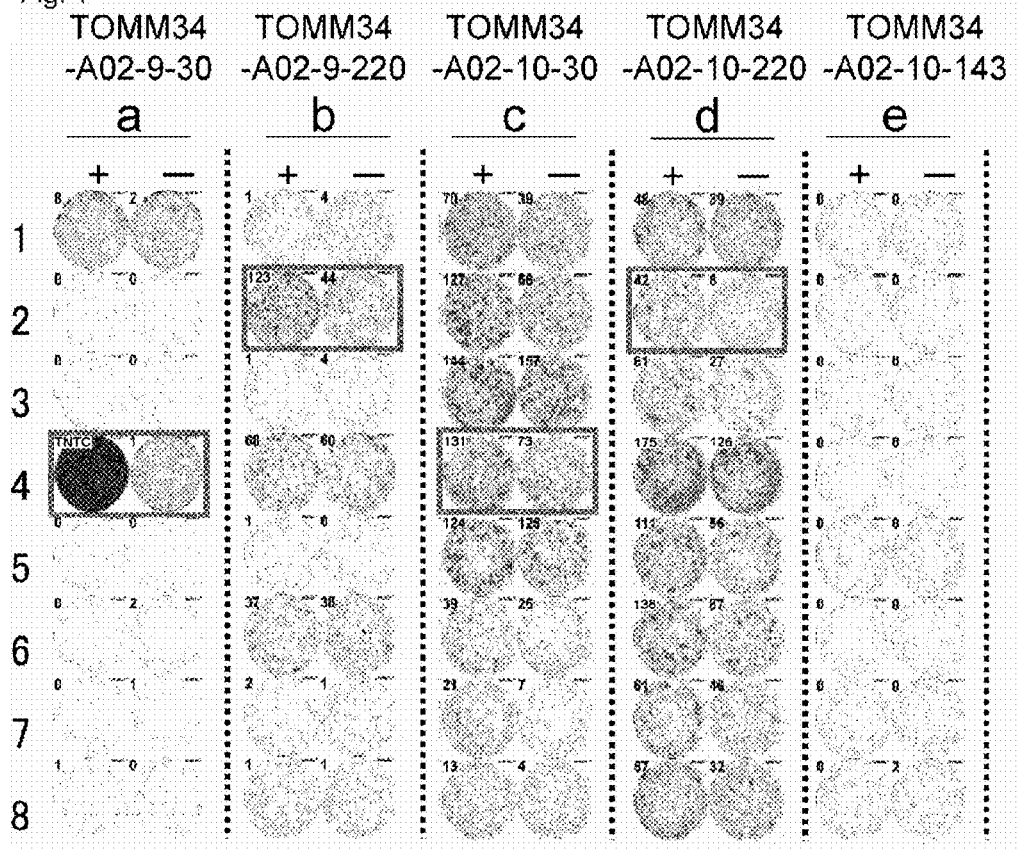
FIG. 1 is composed of a series of photographs, (a)-(e), depicting the results of interferon (IFN)-gamma enzyme-linked immunospot (ELISPOT) assay on CTLs that were induced with peptides derived from TOMM34. The CTLs in well number #4 with TOMM34-A02-9-30 (SEQ ID NO: 1) (a), in #2 with TOMM34-A02-9-220 (SEQ ID NO: 5) (b), in #4 with TOMM34-A02-10-30 (SEQ ID NO: 31) (c) and in #2 with TOMM34-A02-10-220 (SEQ ID NO: 32) (d) showed potent IFN-gamma production as compared with the control, respectively. The square on the well of these pictures indicates that the cells from corresponding well were expanded to establish CTL lines. In contrast, as is the typical case of negative data, specific IFN-gamma production from the CTL stimulated with TOMM34-A02-10-143 (SEQ ID NO: 21) (e) was not shown. In the figures, "+" indicates the IFN-gamma production against target cells pulsed with the appropriate peptide, and "−" indicates the IFN-gamma production against target cells not pulsed with any peptides.

Although any methods and materials similar or equivalent to those described herein can be used in the practice or testing of embodiments of the present invention, the preferred methods, devices, and materials are now described. However, before the present materials and methods are described, it should be understood that these descriptions are merely illustrative and not intended to be limited. It should also be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

All publication, patent or patent application mentioned in this specification are specifically incorporated by reference herein in their entirety. However, nothing herein is to be construed as an admission that the invention is not entitled to antedate such disclosure by virtue of prior invention.

I. DEFINITIONS

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to peptide that are substantially free of cellular material such as carbohydrate, lipid, or other contaminating proteins from the cell or tissue source from which the peptide is derived, or substantially free of chemical precursors or other chemicals when chemically synthesized. The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "oligopeptide" sometimes used in the present specification is used to refer to peptides of the present invention which are 20 residues or fewer, typically 15 residues or fewer in length and is typically composed of between about 8 and about 11 residues, often 9 or 10 residues.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides" and "nucleic acids" are used interchangeably herein and, unless otherwise specifically indicated are similarly to the amino acids referred to by their commonly accepted single-letter codes.

The term "composition" as used herein is intended to encompass a product including the specified ingredients in the specified amounts, as well as any product that results, directly or indirectly, from combination of the specified ingredients in the specified amounts. Such term in relation to "pharmaceutical composition", is intended to encompass a product including the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the term "pharmaceutical composition" refers to any composition made by admixing a compound or substance of the present invention and a pharmaceutically or physiologically acceptable carrier. The phrase "pharmaceutically acceptable carrier" or "physiologically acceptable carrier", as used herein, means a pharmaceutically or physiologically acceptable material, composition, substance, compound or vehicle, including, but are not limited to, a liquid or solid filler, diluent, excipient, solvent or encapsulating material.

The term "active ingredient" herein refers to a substance in a composition that is biologically or physiologically active. Particularly, in the context of pharmaceutical composition, the term "active ingredient" refers to a substance that shows an objective pharmacological effect. For example, in case of pharmaceutical compositions for use in the treatment or prevention of cancer, active ingredients in the compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of CTLs recognizing or killing cancer cells. Before being formulated, the "active ingredient" may also be referred to as "bulk", "drug substance" or "technical product".

Unless otherwise defined, the term "cancer" refers to the cancers over-expressing TOMM34 gene, examples of which include, but are not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor cells, virus-infected cells) and inducing the death of such cells.

Unless otherwise defined, the terms "HLA-A2" refers to the HLA-A2 type containing the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "subject's (or patient's) HLA antigen is HLA-A2" refers to that the subject or patient homozygously or heterozygously possess HLA-A2 antigen gene as the MHC (major histocompatibility complex) Class I molecule, and HLA-A2 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as, reduction in expression of TOMM34 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of post-operative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. PEPTIDES

Peptides of the present invention described in detail below may be referred to as TOMM34 peptide(s).

To demonstrate that peptides derived from TOMM34 function as an antigen recognized by CTLs, peptides derived from TOMM34 (SEQ ID NO: 42) were analyzed to determine whether they were antigen epitopes restricted by HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A2 binding peptides derived from TOMM34 were identified using the information on their binding affinities to HLA-A2. The following candidate peptides were identified;

TOMM34-A02-9-30 (SEQ ID NO: 1),
TOMM34-A02-9-77 (SEQ ID NO: 2),
TOMM34-A02-9-52 (SEQ ID NO: 3),
TOMM34-A02-9-110 (SEQ ID NO: 4),
TOMM34-A02-9-220 (SEQ TD NO: 5),
TOMM34-A02-9-230 (SEQ ID NO: 6),
TOMM34-A02-9-103 (SEQ ID NO: 7),
TOMM34-A02-9-80 (SEQ ID NO: 8),
TOMM34-A02-9-255 (SEQ ID NO: 9),
TOMM34-A02-9-23 (SEQ ID NO: 10),
TOMM34-A02-9-195 (SEQ ID NO: 11),
TOMM34-A02-9-111 (SEQ ID NO: 12),
TOMM34-A02-9-238 (SEQ TD NO: 13),
TOMM34-A02-9-1 (SEQ ID NO: 14),
TOMM34-A02-9-113 (SEQ ID NO: 15),
TOMM34-A02-9-253 (SEQ ID NO: 16),
TOMM34-A02-9-239 (SEQ ID NO: 17),
TOMM34-A02-9-144 (SEQ ID NO: 18),
TOMM34-A02-9-142 (SEQ ID NO: 19),
TOMM34-A02-9-279 (SEQ ID NO: 20),
TOMM34-A02-10-143 (SEQ ID NO: 21),
TOMM34-A02-10-97 (SEQ ID NO: 22),
TOMM34-A02-10-79 (SEQ ID NO: 23),
TOMM34-A02-10-237 (SEQ ID NO: 24),
TOMM34-A02-10-135 (SEQ ID NO: 25),
TOMM34-A02-10-219 (SEQ ID NO: 26),
TOMM34-A02-10-238 (SEQ ID NO: 27),
TOMM34-A02-10-127 (SEQ ID NO: 28),
TOMM34-A02-10-113 (SEQ ID NO: 29),
TOMM34-A02-10-241 (SEQ ID NO: 30),
TOMM34-A02-10-30 (SEQ ID NO: 31),
TOMM34-A02-10-220 (SEQ ID NO: 32),
TOMM34-A02-10-195 (SEQ ID NO: 33),
TOMM34-A02-10-112 (SEQ ID NO: 34),
TOMM34-A02-10-194 (SEQ ID NO: 35)
TOMM34-A02-10-299 (SEQ ID NO: 36)
TOMM34-A02-10-141 (SEQ ID NO: 37)
TOMM34-A02-10-160 (SEQ ID NO: 38)
TOMM34-A02-10-175 (SEQ ID NO: 39) and
TOMM34-A02-10-186 (SEQ ID NO: 40).

Moreover, after in vitro stimulation of T-cells by dendritic cells (DCs) loaded with these peptides, CTLs were successfully established using each of the following peptides;

TOMM34-A02-9-30 (SEQ ID NO: 1),
TOMM34-A02-9-220 (SEQ ID NO: 5),
TOMM34-A02-10-30 (SEQ ID NO: 31) and
TOMM34-A02-10-220 (SEQ ID NO: 32).

These established CTLs showed potent specific CTL activity against target cells pulsed with respective peptides. The results herein demonstrate that TOMM34 is an antigen recognized by CTL and that the peptides tested are epitope peptides of TOMM34 restricted by HLA-A2.

Since the TOMM34 gene is over-expressed in cancer cells and tissues, including, but not limited to, those of AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor but is not expressed in most normal organs, it is a good target for immunotherapy. Thus, the present invention provides nonapeptides (peptides composed of nine amino acid residues) and decapeptides (peptides composed of ten amino acid residues) of CTL-recognized epitopes from TOMM34. Alternatively, the present invention provides an isolated peptide that binds to an HLA antigen and induces cytotoxic T lymphocytes (CTL), wherein the peptide has the amino acid sequence of SEQ ID NO: 42 or is an immunologically active fragment thereof. Specifically, the present invention provides peptides comprising the amino acid sequence selected from among SEQ ID NOs: 1, 5, 31 and 32. More specifically, in some embodiments, the present invention provides peptides consisting of the amino acid sequence selected from among SEQ ID NOs: 1, 5, 31 and 32.

Generally, software programs presently available, for example, on the Internet, such as those described in Parker K C et al., J Immunol 1994, 152(1): 163-75, can be used to calculate the binding affinities between various peptides and HLA antigens in silico. Binding affinity with HLA antigens can be measured as described, for example, in Parker K C et al., J Immunol 1994, 152(1): 163-75; and Kuzushima K et al., Blood 2001, 98(6): 1872-81, Larsen M V et al. BMC Bioinformatics. 2007; 8: 424, and Buus S et al. Tissue Antigens., 62:378-84, 2003. Methods for determining binding affinity are described, for example, in the Journal of Immunological Methods, 1995, 185: 181-190 and Protein Science, 2000, 9: 1838-1846. Therefore, one can readily utilize such software programs to select those fragments derived from TOMM34 that have high binding affinity with HLA antigens. Accordingly, the present invention encompasses peptides composed of any fragments derived from TOMM34 that have high binding affinity with HLA antigens determined by such known programs. Furthermore, such peptides may include the full length sequence of TOMM34 (SEQ ID NO: 42).

The peptides of the present invention, particularly the nonapeptides and decapeptides of the present invention, may be flanked with additional amino acid residues so long as the peptide retains its CTL inducibility. The particular additional amino acid residues may be composed of any kind of amino acids so long as they do not impair the CTL inducibility of the original peptide. Thus, the present invention encompasses peptides having binding affinity for HLA antigens, in particular including peptides derived from TOMM34. Such peptides are, for example, less than about 40 amino acids, often less than about 20 amino acids, usually less than about 15, 14, 13, 12, 11 or 10 amino acids.

Generally, it is known that modifications of one or more amino acids in a peptide do not influence the function of the peptide, or in some cases even enhance the desired function of the original protein. In fact, modified peptides (i.e., peptides composed of an amino acid sequence modified by substituting, deleting, inserting, or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, according to one embodiment of the present invention, the peptide having CTL inducibility of the present invention may be composed of the peptide consisting of the amino acid sequence selected from among SEQ ID NOs: 1, 5, 31 and 32, in which one, two or even more amino acids are added, deleted, inserted and/or substituted.

One of skill in the art will recognize that individual modifications (i.e., deletions, insertions, additions or substitutions) to an amino acid sequence which alters a single amino acid or a small percentage of the overall amino acid sequence results in the conservation of the properties of the original amino acid side-chain; it is thus referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, T, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (T), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, the peptide of the present invention is not restricted thereto and may include non-conservative modifications, so long as the resulting modified peptide retains the CTL inducibility of the original unmodified peptide. Furthermore, the modified peptides do not exclude CTL inducible peptides of polymorphic variants, interspecies homologues, and alleles of TOMM34.

Amino acid residues may be inserted, substituted or added to the peptides of the present invention or, alternatively, amino acid residues may be deleted therefrom to achieve a higher binding affinity. To retain the requisite CTL inducibility, one preferably modifies (i.e., deletes, inserts, adds or substitutes) a small number (for example, 1, 2 or several) or a small percentage of amino acids. Herein, the term "several" means 5 or fewer amino acids, for example, 3 or fewer. The percentage of amino acids to be modified may be 20% or less, for example, 15% or less, for example 10% or less, for example 1 to 5%.

Moreover, the peptides may be substituted or added by such of the amino acid residues to achieve a higher binding affinity. When used in immunotherapy, the present peptides are presented on the surface of a cell or exosome as a complex with an HLA antigen. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity may be introduced into the immunogenic peptides of the present invention.

For example, peptides possessing high HLA-A2 binding affinity tend to have the second amino acid from the N-terminus substituted with leucine or methionine. Likewise, peptides in which the C-terminal is substituted with valine or leucine can also be favorably used. Accordingly, peptides having the amino acid sequences selected from among SEQ ID NOs: 1, 5, 31 and 32 in which the second amino acid from the N-terminus of the amino acid sequence of said SEQ ID NO is substituted with leucine or methionine, and/or the C-terminus of the amino acid sequence of said SEQ ID NO is substituted with valine or leucine are encompassed by the present invention. Substitutions may be introduced not only at the terminal amino acids but also at the position of potential T cell receptor (TCR) recognition of peptides. Several studies have demonstrated that a peptide with amino acid substitutions may be equal to or better than the original, for example CAP1, $p53_{(264-272)}$, Her-2/$neu_{(369-377)}$, or $gp100_{(209-217)}$ (Zaremba et al. Cancer Res. 57, 4570-4577, 1997, T. K. Hoffmann et al. J Immunol. (2002); 168(3): 1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids to the N and/or C-terminus of the present peptides. Such modified peptides with high HLA antigen binding affinity and retained CTL inducibility are also included in the present invention.

For example, the present invention provides an isolated peptide of less than 14, 13, 12, 11, or 10 amino acids in length which binds an HLA antigen, has CTL inducibility, and comprises the amino acid sequence selected from among:

(i) an amino acid sequence is selected from among SEQ ID NOs: 1 and 5;

(ii) an amino acid sequence in which one, two or several amino acid(s) are modified in the amino acid sequence selected from among SEQ ID NOs: 1 and 5, and (iii) the amino acid sequence of (ii), wherein the amino acid sequence has one or both of the following characteristics:

(a) the second amino acid from the N-terminus of said SEQ ID NO is selected from among leucine and methionine; and (b) the C-terminal amino acid of said SEQ ID NO is selected from among valine and leucine.

Moreover, the present invention also provides an isolated peptide of less than 15, 14, 13, 12, or 11 amino acids in length which binds an HLA antigen, has CTL inducibility, and comprises the amino acid sequence selected from among:

(i') an amino acid sequence is selected from among SEQ ID NOs: 31 and 32;

(ii') an amino acid sequence in which one, two or several amino acid(s) are modified in the amino acid sequence selected from the group consisting of SEQ ID NOs: 31 and 32, and (iii') the amino acid sequence of (ii'), wherein the amino acid sequence has one or both of the following characteristics:

(a) the second amino acid from the N-terminus of said SEQ TD NO is selected from among leucine and methionine; and (b) the C-terminal amino acid of said SEQ ID NO is selected from among valine and leucine.

When these peptides are contacted with APCs, those peptides bind with HLA antigens on APCs to be presented on APCs as complexes with HLA antigens. Alternatively, those peptides are introduced into APCs and processed to fragments consisting of an amino acid sequence selected from among (i)-(iii) and (i')-(iii') in APCs to be presented on APCs as complexes with HLA antigens. Consequently, CTLs specific to such peptides are induced.

However, when the peptide sequence is identical to a portion of the amino acid sequence of an endogenous or exogenous protein having a different function, side effects such as autoimmune disorders or allergic symptoms against specific substances may be induced. Therefore, one can perform homology searches using available databases to avoid situations in which the sequence of the peptide matches the amino acid sequence of another protein. When it becomes clear from the homology searches that there exists not even a peptide with 1 or 2 amino acids difference to the objective peptide, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility may be accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive T cells, and then measuring the IFN-gamma produced and released by CTL against the target cells. As the reaction system, transgenic animals that have been produced to express a human HLA antigen (for example, those described in Ben-Mohamed L, Krishnan R, Longmate J, Auge C, Low L, Primus J, Diamond D J, Hum Immunol 2000, 61(8): 764-79, Related Articles, Books, Linkout Induction of CTL response by a minimal epitope vaccine in HLA-A*0201/DR1 transgenic mice: dependence on HLA class II restricted T(H) response) can be used. For example, the target cells may be radiolabeled with $^{51}$Cr and such, and cytotoxic activity may be calculated from radioactivity released from the target cells. Alternatively, it may be examined by measuring IFN-gamma produced and released by CTL in the presence of APCs that carry immobilized peptides, and visualizing the inhibition zone on the media using anti-IFN-gamma monoclonal antibodies.

By examining the CTL inducibility of the peptides as described above, it was discovered that nonapeptides or decapeptides having an amino acid sequence selected from among SEQ ID NOs: 1, 5, 31 and 32 showed particularly high CTL inducibility as well as high binding affinity to an HLA antigen. Thus, these peptides are exemplified as preferred embodiments of the present invention.

Furthermore, homology analyses demonstrated that such peptides do not have significant homology with peptides derived from any other known human gene products. Accordingly, the possibility of unknown or undesired immune responses arising when used for immunotherapy may be lowered. Therefore, also from this aspect, these peptides find use for eliciting immunity in cancer patients against TOMM34. Thus, the preferred peptides of the present invention are those peptides consisting of the amino acid sequence selected from the group consisting of SEQ ID NOs: 1, 5, 31 and 32.

In addition to modifications of the present peptides, discussed above, the peptides of the present invention may also be linked to other peptides, so long as they retain the CTL inducibility, and more preferably also retains the requisite HLA binding. Examples of suitable "other" peptides include: the peptides of the present invention or the CTL inducible peptides derived from other TAAs. The linkers between the peptides are well known in the art, for example, AAY (P. M. Daftarian et al., J Trans Med 2007, 5:26), AAA, NKRK (R. P. M. Sutmuller et al., J Immunol. 2000, 165: 7308-7315) or K (S. Ota et al., Can Res. 62, 1471-1476, K. S. Kawamura et al., J Immunol. 2002, 168: 5709-5715).

For example, non-TOMM34 tumor associated antigen peptides also can be used substantially simultaneously to increase the immune response via HLA class I and/or class II. It is well established that cancer cells can express more than one tumor associated gene. Thus, it is within the scope of routine experimentation for one of ordinary skill in the art to determine whether a particular subject expresses additional tumor associated genes, and then include HLA class I and/or HLA class II binding peptides derived from expression products of such genes in TOMM34 compositions or vaccines.

Examples of HLA class I and HLA class II binding peptides are known to those of ordinary skill in the art (for example, see Coulie, Stem Cells 13:393-403, 1995), and thus can be used in the invention in a like manner as those disclosed herein. Thus, one of ordinary skill in the art can readily prepare polypeptides including one or more TOMM34 peptides and one or more of the non-TOMM34 peptides, or nucleic acids encoding such polypeptides, using standard procedures of molecular biology.

The above described peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci USA 92(13):5845-5849, 1995; Gilbert et al., Nature Biotechnol. 15(12):1280-1284, 1997; Thomson et al., J Immunol. 157(2):822-826, 1996; Tam et al., J Exp. Med. 171(1):299-306, 1990). Polytopes containing various numbers and combinations of epitopes can be prepared and tested for recognition by CTLs and for efficacy in increasing an immune response.

The peptides of the present invention may be further linked to other substances, so long as they retain the CTL inducibility of the original peptide. Examples of suitable substances may include: peptides, lipids, sugar and sugar chains, acetyl groups, natural and synthetic polymers, etc. The peptides may contain modifications such as glycosylation, side chain oxidation, or phosphorylation; so long as the modifications do not destroy the biological activity of the peptides as described herein. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adopted for the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted, inserted or added by one, two or several amino acid residues, those having same or higher activity as compared to original peptides can be screened for or selected. The present invention, therefore, also provides the method of screening for or selecting modified peptides having same or higher activity as compared to originals. For example, the method may include steps of:

a: substituting, deleting, inserting, or adding at least one amino acid residue of a peptide of the present invention, b: determining the activity of said peptide, and c: selecting the peptide having same or higher activity as compared to the original.

Herein, said activity may include MHC binding activity, APC or CTL inducibility and cytotoxic activity.

When the peptides of the present intention include a cysteine residue, the peptides tend to form dimers via a disulfide bond between SH groups of the cysteine residues. Therefore, dimers of the peptide of the present invention are also included in the peptides of the present invention.

III. PREPARATION OF TOMM34 PEPTIDES

The peptides of the present invention may be prepared using well known techniques. For example, the peptides may be prepared synthetically, by recombinant DNA technology or chemical synthesis. The peptides of the present invention may be synthesized individually or as longer polypeptides including two or more peptides. The peptides may be isolated, i.e., purified or isolated substantially free of other naturally occurring host cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

A peptide of the present invention may be obtained through chemical synthesis based on the selected amino acid sequence. For example, conventional peptide synthesis methods that may be adopted for the synthesis include:

(i) Peptide Synthesis, Interscience, New York, 1966;

(ii) The Proteins, Vol. 2, Academic Press, New York, 1976;

(iii) Peptide Synthesis (in Japanese), Maruzen Co., 1975;

(iv) Basics and Experiment of Peptide Synthesis (in Japanese), Maruzen Co., 1985;

(v) Development of Pharmaceuticals (second volume) (in Japanese), Vol. 14 (peptide synthesis), Hirokawa, 1991;

(vi) WO99/67288; and (vii) Barmy G. & Merrifield R. B., Peptides Vol. 2, "Solid Phase Peptide Synthesis", Academic Press, New York, 1980, 100-118.

Alternatively, the present peptides may be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. POLYNUCLEOTIDES

The present invention provides polynucleotide that encode any of the aforementioned peptides of the present invention. These include polynucleotides derived from the natural occurring TOMM34 gene (for example, SEQ ID NO: 42 (GenBank Accession No. NM_006809)) and those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) may be modified to yield a functionally identical molecule. Accordingly, each silent variation of a nucleic acid that encodes a peptide is implicitly described in each disclosed sequence.

The polynucleotide of the present invention may be composed of DNA, RNA, and derivatives thereof. As is well known in the art, a DNA molecule is composed of bases such as the naturally occurring bases A, T, C, and G, and T is replaced by U in an RNA. One of skill will recognize that non-naturally occurring bases be included in polynucleotides, as well.

The polynucleotide of the present invention may encode multiple peptides of the present invention with or without intervening amino acid sequences. For example, the intervening amino acid sequence may provide a cleavage site (e.g., enzyme recognition sequence) of the polynucleotide or the translated peptides. Furthermore, the polynucleotide may include any additional sequences to the coding sequence encoding the peptide of the present invention. For example, the polynucleotide may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, a polynucleotide may be produced by insertion into an appropriate vector, which may be expressed when transfected into a competent cell. Alternatively, a polynucleotide may be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide may be synthesized using the solid phase techniques, as described in Beaucage S L & Iyer R P, Tetrahedron 1992, 48: 2223-311; Matthes et al., EMBO J 1984, 3: 801-5.

V. EXOSOMES

The present invention further provides intracellular vesicles, referred to as exosomes, that present complexes formed between the peptides of this invention and HLA antigens on their surface. Exosomes may be prepared, for example, using the methods detailed in Japanese Patent Application Kohyo Publications Nos. Hei 11-510507 and WO99/03499, and may be prepared using APCs obtained from patients who are subject to treatment and/or prevention. The exosomes of this invention may be inoculated as vaccines, similarly to the peptides of this invention.

The type of HLA antigens included in the complexes must match that of the subject requiring treatment and/or prevention. For example, for in the Japanese population, HLA-A2, particularly HLA-A*0201 and HLA-A*0206, are quite prevalent and therefore would be appropriate for treatment of Japanese patients. The use of HLA-A2 type that is highly expressed among the Japanese and Caucasian populations is favorable for obtaining effective results, and subtypes such as HLA-A*0201 and HLA-A*0206 find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution, deletion, insertion or addition of one, two, or several amino acids may be performed based on the amino acid sequence of the naturally occurring TOMM34 partial peptide.

When the exosome of the present invention possess HLA-A2 type as an HLA antigen, the peptides including the amino acid sequence selected from among SEQ ID NOs: 1, 5, 31 and 32 have particular utility.

VI. ANTIGEN-PRESENTING CELLS (APCS)

The present invention also provides isolated antigen-presenting cells (APCs) that present complexes formed between HLA antigens and the peptides of this invention on its surface. The APCs may be derived from patients who are subject to treatment and/or prevention, and may be administered as vaccines by themselves or in combination with other drugs including the peptides of this invention, exosomes, or CTLs.

The APCs are not limited to a particular kind of cells. Examples of APCs include, but are not limited to, dendritic cells (DCs), Langerhans cells, macrophages, B cells, and activated T cells, which are known to present proteinaceous antigens on their cell surface so as to be recognized by lymphocytes. Since DCs are a representative APCs having the strongest CTL inducing action among APCs, DCs find use as the APCs of the present invention.

For example, the APCs of the present invention may be obtained by inducing DCs from peripheral blood monocytes and then contacting (stimulating) them with the peptides of this invention in vitro, ex vivo or in vivo. When the peptides of this invention are administered to the subjects, APCs that present the peptides of this invention are induced in the body of the subject. The phrase "inducing an APC" includes contacting (stimulating) a cell with the peptides of the present invention, or introducing a polynucleotide encoding the peptides of the present invention into a cell to present a complex formed between an HLA antigen and the peptides of the present invention on cell's surface. Therefore, the APCs of this invention may be obtained by collecting the APCs from the subject after administering the peptides of this invention to the subject. Alternatively, the APCs of this invention may be obtained by contacting APCs collected from a subject with the peptide of this invention.

The APCs of the present invention may be administered to a subject for inducing immune response against cancer in the subject by themselves or in combination with other drugs including the peptides, exosomes or CTLs of this invention. For example, the ex vivo administration may include steps of:

a: collecting APCs from a first subject,
b: contacting with the APCs of step a, with the peptide, and
c: administering the APCs of step b to a second subject.

The first subject and the second subject may be the same individual, or may be different individuals. The APCs obtained by step b may serve as a vaccine for the treatment and/or prevention of a cancer, examples of which include, but are not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

In the context of the present invention, one may utilize the peptides of the present invention for manufacturing a pharmaceutical composition or agent capable of inducing antigen-presenting cells. A method or process for manufacturing a pharmaceutical composition or agent for inducing antigen-presenting cells is provided herein and preferably includes the step of admixing or formulating the peptide of the invention with a pharmaceutically acceptable carrier.

The present invention also provides for the use of the peptides of the present invention for inducing antigen-presenting cells.

According to an aspect of the present invention, the APCs of the present invention have a high level of CTL inducibility. In the phrase "high level of CTL inducibility", the high level means that CTL inducibility is relatively high as compared to the level of that detected in APCs contacted with no peptide. Such APCs having a high level of CTL inducibility may be prepared by a method which includes the step of transferring a polynucleotide encoding the peptide of this invention to APCs in vitro as well as the method mentioned above. The introduced polynucleotides may be in the form of DNAs or RNAs. Examples of methods for introduction include, without particular limitations, various methods conventionally performed in this field, such as lipofection, electroporation, and calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene encoding the peptide of the present invention into APCs, the gene undergoes transcription, translation, and such in the cell, and then the obtained protein is processed by MHC Class I or Class II, and proceeds through a presentation pathway to present the peptides of the present invention.

Alternatively, the APCs of the present invention can be prepared by a method which includes the step of contacting APCs with the peptide of the present invention. In some embodiments, the APCs of the present invention present complexes of HLA-A2 antigen and the peptide of the present invention on their surface.

VII. CYTOTOXIC T LYMPHOCYTES (CTLS)

A CTL induced against any of the peptides of the present invention strengthens the immune response targeting cancer cells in vivo and thus may be used as vaccines similar to the peptides per se. Thus, the present invention provides isolated CTLs that are specifically induced or activated by any of the present peptides.

Such CTLs may be obtained by (1) administering the peptide(s) of the present invention to a subject, (2) contacting (stimulating) subject-derived APCs and CD8-positive T cells, or peripheral blood mononuclear leukocytes in vitro with the peptide(s) of the present invention, (3) contacting CD8-positive T cells or peripheral blood mononuclear leukocytes in vitro with the APCs or exosomes presenting a complex of an HLA antigen and the peptide of the present invention on its surface or (4) introducing a polynucleotide/polynucleotides encoding T cell receptor (TCR) subunits, wherein the TCR formed by such TCR subunits is capable of binding to a complex of an HLA antigen and the peptide of this invention on a cell surface. Such APCs or exosomes for the method of (3) can be prepared by the methods described above. Details of the method of (4) is described bellow in section "VIII. T cell receptor (TCR)".

The CTLs of the present invention may be derived from patients who are subject to treatment and/or prevention, and may be administered by themselves or in combination with other drugs including the peptides of this invention or exosomes for the purpose of regulating effects. The obtained CTLs act specifically against target cells presenting the peptides of this invention, for example, the same peptides used for induction. The target cells may be cells that endogenously express TOMM34, such as cancer cells, or cells that are transfected with the TOMM34 gene; and cells that present a peptide of this invention on the cell surface due to stimulation by the peptide may also serve as targets of activated CTL attack.

In some embodiments, the CTLs of the present invention are CTLs that recognize cells presenting complexes of an HLA-A2 antigen and the peptide of the present invention on their surface. In the context of the CTL, the phrase "recognize a cell" refers to binding a complex of an HLA-A2 antigen and the peptide of the present invention on the cell surface via its TCR and showing specific cytotoxic activity against the cell. Herein, "specific cytotoxic activity" refers to showing cytotoxic activity against the cell presenting a complex of an HLA-A2 antigen and the peptide of the present invention but not other cells.

VIII. T CELL RECEPTOR (TCR)

The present invention also provides a composition including a polynucleotide/polynucleotides encoding polypeptides that are capable of forming a subunit of a T cell receptor (TCR), and methods of using the same. Such TCR subunits have the ability to form TCRs that confer specificity against tumor cells expressing TOMM34 to T cells. By using the known methods in the art, the polynucleotide/polynucleotides encoding each of alpha- and beta-chains of the TCR subunits of the CTL induced with the peptides of the present invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') (SEQ ID NO: 43) as 5' side primers and 3-TRa-C primers (5'-tcagctggaccacagccgcagcgt-3') (SEQ ID NO: 44) specific to TCR alpha chain C region, 3-TRb-C1 primers (5'-tcagaaatccttctcttgac-3') (SEQ ID NO: 45) specific to TCR beta chain C1 region or 3-TRbeta-C2 primers (5'-ctagcctctggaatccttctctt-3') (SEQ ID NO: 46) specific to TCR beta chain C2 region as 3' side primers, but not limited thereto. The derivative TCRs can bind target cells presenting the TOMM34 peptide of the present invention with high avidity, and optionally mediate efficient killing of target cells presenting the TOMM34 peptide of the present invention in vivo and in vitro.

The polynucleotide/polynucleotides encoding the TCR subunits (i.e., the polynucleotide encoding both of the TCR subunits or polynucleotides encoding each of the TCR subunits) may be incorporated into suitable vectors, e.g., retroviral vectors. These vectors are well known in the art. The polynucleotide or the vectors including them usefully may be transferred into a T cell (e.g., CD8-positive T cell), for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR against the peptide of the present invention is a receptor capable of specifically recognizing a complex of a peptide of the present invention and HLA antigen, giving a T cell specific activity against a target cell presenting a complex of the peptide of the present invention and an HLA antigen when the TCR is expressed on the surface of the T cell. It can be confirmed by any known methods that CTLs prepared by introducing the polypeptide(s) encoding such TCR subunits can be specifically recognize such target cells. Preferred examples of such methods include, for example, tetramer analysis using HLA molecule and the peptide of the present invention, and ELISPOT assay. By ELISPOT assay, it can be confirmed that CTL prepared by the method described above can specifically recognizes the target cells and that the signals generated by such recognition can be transmitted intracellularly. Furthermore, it can be also confirmed by known methods that CTLs prepared by the method described above have specific cytotoxic activity against the target cells. Examples of such methods include, for example, chromium release assay using cells expressing both of HLA-A2 antigen and TOMM34.

In one aspect, the present invention provides CTLs that are prepared by transduction with the polynucleotide/polynucleotides encoding the TCR subunits polypeptides (i.e., the polynucleotide encoding both of the TCR subunits or polynucleotides encoding each of the TCR subunits), wherein the TCR formed by such TCR subunits can bind to a complex of the TOMM34 peptide having an amino acid sequence selected from among SEQ ID NOs: 1, 5, 31 and 32 and HLA-A2 antigen on a cell surface.

The transduced CTLs are capable of homing to cancer cells in vivo, and may be expanded by well known culturing methods in vitro (e.g., Kawakami et al., J Immunol., 142, 3452-3461 (1989)). The CTLs of the present invention may be used to form an immunogenic composition useful in either or both of the treatment and the prevention of cancer in a patient in need of therapy or protection (WO2006/031221).

IX. PHARMACEUTICAL AGENTS OR COMPOSITIONS

Since TOMM34 expression is specifically elevated in cancer, examples of which include, but not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor as compared with normal tissue, the peptides of or polynucleotides of the present invention may be used for the treatment and/or prophylaxis of cancer, and/or the prevention of a postoperative recurrence thereof. Thus, the present invention provides a pharmaceutical agent or composition formulated for the treatment and/or prophylaxis of cancer, and/or for the prevention of a postoperative recurrence thereof, such composition including as an active ingredient one or more of the peptides, or polynucleotides of this invention as an active ingredient. Alternatively, the present peptides may be expressed on the surface of any of the foregoing exosomes or cells, such as APCs for the use as pharmaceutical agents or compositions. In addition, the aforementioned CTLs which target any of the peptides of the present invention may also be used as the active ingredient of the present pharmaceutical agents or compositions.

The pharmaceutical compositions of the present invention also find use as a vaccine. In the context of the present invention, the phrase "vaccine" (also referred to as an "immunogenic composition") refers to a composition that has the function to improve, enhance, and/or induce anti-tumor immunity upon inoculation into animals.

The pharmaceutical compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient in manufacturing a pharmaceutical composition or agent for treating cancer or tumor, said active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

Alternatively, the present invention further provides an active ingredient for use in the treatment and/or prevention of cancers or tumors, said active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

Alternatively, the present invention further provides a method or process for manufacturing a pharmaceutical composition or agent for treating or preventing cancer or tumor, wherein the method or process includes the step of formulating a pharmaceutically or physiologically acceptable carrier with an active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

In another embodiment, the present invention also provides a method or process for manufacturing a pharmaceutical composition or agent for treating or preventing cancer or tumor, wherein the method or process includes the steps of admixing an active ingredient with a pharmaceutically or physiologically acceptable carrier, wherein the active ingredient is selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

The pharmaceutical agents or compositions of the present invention may be used to treat and/or prevent cancer, and/or to prevent a postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, peptides including the amino acid sequence selected from among SEQ ID NO: 1, 5, 31 and 32 have been found to be HLA-A2 restricted epitope peptides or the candidates that may induce potent and specific immune response. Therefore, the present pharmaceutical agents or compositions which include any of these peptides with the amino acid sequences of SEQ ID NOs: 1, 5, 31 and 32 are particularly suited for the administration to subjects whose HLA antigen is HLA-A2. The same applies to pharmaceutical agents or compositions which include polynucleotides encoding any of these peptides (i.e., the polynucleotides of this invention).

Cancers to be treated by the pharmaceutical agents or compositions of the present invention are not limited and include any cancer in which TOMM34 is involved (e.g., is over-expressed), including, but not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

The pharmaceutical agents or compositions of the present invention may contain in addition to the aforementioned active ingredients, other peptides that have the ability to induce CTLs against cancerous cells, other polynucleotides encoding the other peptides, other cells that present the other peptides, or such. Examples of such "other" peptides having the ability to induce CTLs against cancerous cells include, but are not limited to, cancer specific antigens (e.g., identified TAAs).

If necessary, the pharmaceutical agents or compositions of the present invention may optionally include other therapeutic substances as an active ingredient, so long as the substance does not inhibit the antitumoral effect of the active ingredient, e.g., any of the present peptides. For example, formulations may include anti-inflammatory substances or compositions, pain killers, chemotherapeutics, and the like. In addition to including other therapeutic substances in the medicament itself, the medicaments of the present invention may also be administered sequentially or concurrently with the one or more other pharmacologic compositions. The amounts of medicament and pharmacologic composition depend, for example, on what type of pharmacologic composition(s) is/are used, the disease being treated, and the scheduling and routes of administration.

Those of skill in the art will readily recognize that, in addition to the ingredients particularly mentioned herein, the pharmaceutical agents or compositions of the present invention may further include other substances conventional in the art having regard to the type of formulation in question (e.g., fillers, binders, diluents, etc.).

In one embodiment of the present invention, the present pharmaceutical agents or compositions may be packaged in articles of manufacture, e.g., as kits containing materials useful for treating the pathological conditions of the disease to be treated, e.g., cancer. The article of manufacture may include a container of any of the present pharmaceutical agents or compositions with a label. Suitable containers include bottles, vials, and test tubes. The containers may be formed from a variety of materials, such as glass or plastic. The label on the container should indicate the agent or composition is used for treating or prevention of one or more conditions of the disease. The label may also indicate directions for administration and so on.

In addition to the container described above, a kit including a pharmaceutical agent or composition of the present invention may optionally further include a second container housing a pharmaceutically-acceptable diluent. It may further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptides of this invention can be administered directly as a pharmaceutical agent or composition, or if necessary, may be formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of this invention can be used for anticancer purposes.

The peptides of this invention can be prepared in a combination, which includes two or more of peptides of the present invention, to induce CTL in vivo. The peptides can be in a cocktail or can be conjugated to each other using standard techniques. For example, the peptides can be chemically linked or expressed as a single fusion polypeptide sequence that may have one or several amino acid as a linker (e.g., Lysine linker: K. S. Kawamura et al. J. Immunol. 2002, 168: 5709-5715). The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of this invention on their cell surface. These APCs are readministered to the subjects to induce CTLs in the subjects, and as a result, aggressiveness towards the tumor-associated endothelium can be increased.

The pharmaceutical agents or compositions for treating and/or prevention of cancer, that include any peptide of this invention as the active ingredient, can additionally include an adjuvant so that cellular immunity will be established effectively, or they can be administered with other active ingredients, and they can be administered by formulation into granules. An adjuvant refers to a compound that enhances the immune response against the protein when administered together (or successively) with the protein having immunological activity. An adjuvant that can be applied includes those described in the literature (Clin Microbiol Rev 1994, 7: 277-89). Exemplary adjuvants include aluminum phosphate, aluminum hydroxide, alum, cholera toxin, *salmonella* toxin, Incomplete Freund's adjuvant (IFA), Complete Freund's adjuvant (CFA), IS-COMatrix, GM-CSF, CpG, O/W emulsion, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid. As used herein, the phrase "pharmaceutically acceptable salt" refers to those salts that retain the biological effectiveness and properties of the compound and that are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical agents or compositions of the present invention may further include a component which primes CTL. Lipids have been identified as substances or compositions capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

Examples of suitable methods of administration include, but are not necessarily limited to, oral, intradermal, subcutaneous, intramuscular, intraosseous, peritoneal, and intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1,000 mg, for example, 0.01 mg to 100 mg, for example, 0.1 mg to 10 mg, for example, 0.5 mg to 5 mg and can be administered once in a few days to few months. One skilled in the art can appropriately select a suitable dose.

(2) Pharmaceutical Agents or Compositions Containing Polynucleotides as the Active Ingredient The pharmaceutical agents or compositions of the present invention can also include nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella* typhi vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al. in Current Protocols in Molecular Biology, John Wiley & Sons, N Y, 1993; and Krieger in Gene Transfer and Expression, A Laboratory Manual, Stockton Press, N Y, 1990.

Like administration of peptides, administration of polynucleotides may be performed oral, intradermal, subcutaneous, intraosseous, peritoneal and/or intravenous injection, or such, e.g., systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg and can be administered once every a few days to once every few months. One skilled in the art can appropriately select the suitable dose.

X. METHODS USING THE PEPTIDES, EXOSOMES, APCS AND CTLS

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the additional compounds do not inhibit their CTL inducibility. Thus, any of the aforementioned pharmaceutical agents or compositions of the present invention can be used for inducing CTLs. In addition thereto, those including the peptides and polynucleotides can be also used for inducing APCs as explained below.

(1) Method of Inducing Antigen-Presenting Cells (APCs)

The present invention provides methods of inducing APCs with high CTL inducibility using the peptides or polynucleotides of this invention.

The methods of the present invention include the step of contacting APCs with the peptides of this invention in vitro, ex vivo or in vivo. For example, the method contacting APCs with the peptides ex vivo can include steps of:

a: collecting APCs from a subject, and b: contacting the APCs of step a with the peptide of the present invention.

The APCs are not limited to a particular kind of cells. Examples of APCs include, but are not limited to DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or with other peptides of this invention.

On the other hand, when the peptides of the present invention are administered to a subject, the APCs are contacted with the peptides in vivo, consequently, the APCs with high CTL inducibility are induced in the body of the subject. Thus, the method of the present invention may include administering the peptides of this invention to a subject. Similarly, when the polynucleotides of this invention are administered to a subject in an expressible form, the peptides of this invention are expressed and contacted with APCs in vivo, consequently, the APCs with high CTL inducibility are induced in the body of the subject. Thus, instead of the aforementioned step, the method of the present invention may include administering the polynucleotides of this invention to a subject. "Expressible form" is described above in section "IX. Pharmaceutical agents or compositions, (2) Pharmaceutical agents or compositions containing polynucleotides as the active ingredient".

Alternatively, the method of the present invention may include introducing the polynucleotide of this invention into an APC to induce an APC with CTL inducibility. For example, the method can include steps of:

a: collecting APCs from a subject, and b: introducing a polynucleotide encoding the peptide of this invention.

Step b can be performed as described above in section "VI. Antigen-presenting cells".

Alternatively, the present invention provides a method for preparing an antigen-presenting cell (APC) which specifically induces CTL activity against TOMM34, wherein the method includes one of the following steps:

(a) contacting an APC with a peptide of the present invention in vitro, ex vivo or in vivo; and (b) introducing a polynucleotide encoding a peptide of the present invention into an APC.

Alternatively, the present invention provides methods for inducing an APC having CTL inducibility, wherein the methods include the step selected from the group consisting of:

(a) contacting an APC with the peptide of the present invention, and (b) introducing the polynucleotide encoding the peptide of the present invention into an APC.

The methods of the present invention can be carried out in vitro, ex vivo or in vivo. Preferably, the methods of the present invention can be carried out in vitro or ex vivo. APCs used for induction of APCs having CTL inducibility can be preferably APCs expressing HLA-A2 antigen. Such APCs can be prepared by the methods well-known in the arts from peripheral blood mononuclear cells (PBMCs) obtained from a subject whose HLA antigen is HLA-A2. The APCs induced by the method of the present invention can be APCs that present a complex of the peptide of the present invention and HLA antigen (HLA-A2 antigen) on its surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having CTL inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having CTL inducibility.

(2) Method of Inducing CTLs

The present invention also provides methods for inducing CTLs using the peptides, polynucleotides, or exosomes or APCs of this invention.

The present invention also provides methods for inducing CTLs using a polynucleotide/polynucleotides encoding polypeptides (i.e., TCR subunits) that is capable of forming a T cell receptor (TCR) that is capable of recognizing a complex of the peptides of the present invention and HLA antigens. Preferably, the methods for inducing CTLs include at least one step selected from among:

a) contacting a CD8-positive T cell with an antigen-presenting cell and/or an exosome that presents on its surface a complex of an HLA antigen and a peptide of the preset invention; and b) introducing a polynucleotide/polynucleotides encoding polypeptides that are capable of forming a TCR that is capable of recognizing a complex of a peptide of the present invention and an HLA antigen into a CD8-positive T cell.

When the peptides, the polynucleotides, APCs, or exosomes of this invention are administered to a subject, CTL is induced in the body of the subject, and the strength of the immune response targeting the cancer cells is enhanced. Thus, instead of aforementioned step, the methods of the present invention may include the step of administering the peptides, the polynucleotides, the APCs or exosomes of this invention to a subject.

Alternatively, CTL can be also induced by using them ex vivo, and after inducing CTL, the activated CTLs are returned to the subject. For example, the method can include steps of:

a: collecting APCs from subject, b: contacting with the APCs of step a, with the peptide of the present invention, and c: co-culturing the APCs of step b with CD8-positive T cells.

The APCs to be co-cultured with the CD8-positive T cells in above step c can also be prepared by transferring a gene that includes a polynucleotide of this invention into APCs as described above in section "VI. Antigen-presenting cells", although the present invention is not limited thereto and encompasses any APC that effectively presents the present on its surface a complex of an HLA antigen and a peptide of this invention.

One may optionally utilize the exosomes that presents on its surface a complex of an HLA antigen and the peptide of this invention instead of the aforementioned APCs. Namely, the present invention can includes the step of co-culturing exosomes presenting on its surface a complex of an HLA antigen and the peptide of this invention. Such exosomes can be prepared by the methods described above in section "V. Exosomes".

Furthermore, the CTL of the present invention can be induced by introducing into a CD8-positive T cell a polynucleotide/polynucleotides encoding the TCR subunits, wherein the TCR formed by such TCR subunits is capable of binding to a complex of an HLA antigen and the peptide of this invention on a cell surface. Such transduction can be performed as described above in section "VIII. T cell receptor (TCR)".

The methods of the present invention can be carried out in vitro, ex vivo or in vivo. Preferably, the methods of the present invention can be carried out in vitro or ex vivo. CD8-positive T cells used for induction of CTLs can be prepared by well-known methods in the art from PBMCs obtained from a subject. In preferred embodiments, the donor for CD8-positive T cells can be a subject whose HLA antigen is HLA-A2. The CTLs induced by the methods of the present invention can be CTLs that can recognize cells presenting a complex of the peptide of the present invention and HLA antigen on its surface. When CTLs induced by the method of the present invention are administered to a subject in order to induce immune responses against cancer in the subject, the subject is preferably the same one from whom CD8-positive T cells are derived. However, the subject may be a different one from the CD8-positive T cell donor so long as the subject has the same HLA type with the CD8-positive T cell donor.

In addition, the present invention provides a method or process for manufacturing a pharmaceutical composition inducing CTLs, wherein the method includes the step of admixing or formulating the peptide of the present invention with a pharmaceutically acceptable carrier.

In another embodiment, the present invention provide an agent or composition for inducing CTL, wherein the agent or composition comprises one or more peptide(s), one or more polynucleotide(s), or one o more APCs or exosomes of the present invention.

In another embodiment, the present invention provides the use of the peptide, the polynucleotide, or APC or exosome of the present invention in the manufacture of an agent or composition formulated for inducing a CTL.

Alternatively, the present invention further provides the peptide, the polynucleotide, or APC or exosome of the present invention for use in inducing a CTL.

(3) Method of Inducing Immune Response

Moreover, the present invention provides methods for an inducing immune response against diseases related to TOMM34. Suitable diseases include cancer, examples of which include, but are not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

The methods of the present invention include the step of administering agents or compositions containing any of the peptides of the present invention or polynucleotides encoding them. Alternatively, the method of the present invention may include the step of administering exosomes or APCs presenting any of the peptides of the present invention. For details, see the item of "IX. Pharmaceutical agents or compositions", particularly the part describing the use of the pharmaceutical agents or compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical agent or composition inducing immune response, wherein the method includes the step of admixing or formulating the peptide of the present invention with a pharmaceutically acceptable carrier.

Alternatively, the method of the present invention may include the step of administrating a vaccine or a pharmaceutical composition of the present invention that contains:

(a) a peptide of the present invention;
(b) a nucleic acid encoding such a peptide as disclosed herein in an expressible form;
(c) an APC or an exosome presenting a peptide of the present invention on its surface; or
(d) a cytotoxic T cell of the present invention.

In the context of the present invention, cancer over-expressing TOMM34 can be treated with these active ingredients. Examples of such cancer includes, but is not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor. Accordingly, prior to the administration of the vaccines or pharmaceutical compositions including the active ingredients, it is preferable to confirm whether the expression level of TOMM34 in the cells or tissues to be treated is enhanced compared with normal cells of the same organ. Thus, in one embodiment, the present invention provides a method for treating cancer (over)expressing TOMM34, which method may include the steps of:

i) determining the expression level of TOMM34 in cells or tissue(s) obtained from a subject with the cancer to be treated;
ii) comparing the expression level of TOMM34 with normal control; and
iii) administrating at least one component selected from among (a) to (d) described above to a subject with cancer over-expressing TOMM34 compared with normal control.

Alternatively, the present invention provides a vaccine or pharmaceutical composition that includes at least one component selected from among (a) to (d) described above, for use in administrating to a subject having cancer over-expressing TOMM34. In other words, the present invention further provides a method for identifying a subject to be treated with a TOMM34 polypeptide of the present invention, such method including the step of determining an expression level of TOMM34 in subject-derived cells or tissue(s), wherein an increase of the level compared to a normal control level of the gene indicates that the subject has cancer which may be treated with the TOMM34 polypeptide of the present invention. The methods of treating cancer of the present invention are described in more detail below.

Any subject-derived cell or tissue can be used for the determination of TOMM34 expression so long as it includes the objective transcription or translation product of TOMM34. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of TOMM34 in cells or tissues obtained from a subject is determined. The expression level can be determined at the transcription (nucleic acid) product level, using methods known in the art. For example, the mRNA of TOMM34 may be quantified using probes by hybridization methods (e.g., Northern hybridization). The detection may be carried out on a chip or an array. The use of an array is preferable for detecting the expression level of TOMM34. Those skilled in the art can prepare such probes utilizing the sequence information of TOMM34. For example, the cDNA of TOMM34 may be used as the probes. If necessary, the probes may be labeled with a suitable label, such as dyes, fluorescent substances and isotopes, and the expression level of the gene may be detected as the intensity of the hybridized labels.

Furthermore, the transcription product of TOMM34 may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of TOMM34. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including a TOMM34 sequence, or an anti sense strand nucleotide sequence of a nucleic acid including a TOMM34 sequence, or of a naturally occurring mutant of these sequences. In particular, for example, in a preferred embodiment, an oligonucleotide having 5-50 in length can be used as a primer for amplifying the genes, to be detected. More preferably, mRNA or cDNA of a TOMM34 gene can be detected with oligonucleotide probe or primer of a specific size, generally 15-30b in length. The size may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides. In preferred embodiments, length of the oligonucleotide probe or primer can be selected from 15-25. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product may be detected for the diagnosis of the present invention. For example, the quantity of TOMM34 protein (SEQ ID NO: 42) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the TOMM34 protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of TOMM34 gene based on its translation product, the intensity of staining may be measured via immunohistochemical analysis using an antibody against the TOMM34 protein. Namely, in this measurement, strong staining indicates increased presence/level of the protein and, at the same time, high expression level of TOMM34 gene.

The expression level of a target gene, e.g., the TOMM34 gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

The control level may be determined at the same time with the cancer cells by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of TOMM34 gene in samples from subjects whose disease states are known. Furthermore, the control level can be derived from a database of expression patterns from previously tested cells. Moreover, according to an aspect of the present invention, the expression level of TOMM34 gene in a biological sample may be compared to multiple control levels, determined from multiple reference samples. It is preferred to use a control level determined from a reference sample derived from a tissue type similar to that of the subject-derived biological sample. Moreover, it is preferred to use the standard value of the expression levels of TOMM34 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level".

When the expression level of TOMM34 gene is increased as compared to the normal control level, or is similar/equivalent to the cancerous control level, the subject may be diagnosed with cancer to be treated.

The present invention also provides a method of (i) diagnosing whether a subject has the cancer to be treated, and/or (ii) selecting a subject for cancer treatment, which method includes the steps of:

a) determining the expression level of TOMM34 in cells or tissue(s) obtained from a subject who is suspected to have the cancer to be treated;

b) comparing the expression level of TOMM34 with a normal control level;

c) diagnosing the subject as having the cancer to be treated, if the expression level of TOMM34 is increased as compared to the normal control level; and d) selecting the subject for cancer treatment, if the subject is diagnosed as having the cancer to be treated, in step c).

Alternatively, such a method includes the steps of:

a) determining the expression level of TOMM34 in cells or tissue(s) obtained from a subject who is suspected to have the cancer to be treated;

b) comparing the expression level of TOMM34 with a cancerous control level;

c) diagnosing the subject as having the cancer to be treated, if the expression level of TOMM34 is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from cancer that can be treated with the TOMM34 polypeptide of the present invention, which may also be useful in assessing the prognosis of cancer and/or monitoring the efficacy or applicability of a cancer therapy, particularly a cancer immunotherapy. Illustrative examples of suitable cancers include, but are not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor. More particularly, the kit preferably includes at least one reagent for detecting the expression of the TOMM34 gene in a subject-derived cell, such reagent selected from the group of:

(a) a reagent for detecting mRNA of the TOMM34 gene;
(b) a reagent for detecting the TOMM34 protein or the immunologically fragment thereof; and
(c) a reagent for detecting the biological activity of the TOMM34 protein.

Examples of reagents suitable for detecting mRNA of the TOMM34 gene include nucleic acids that specifically bind to or identify the TOMM34 mRNA, such as oligonucleotides that have a complementary sequence to a portion of the TOMM34 mRNA. These kinds of oligonucleotides are exemplified by primers and probes that are specific to the TOMM34 mRNA. These kinds of oligonucleotides may be prepared based on methods well known in the art. If needed, the reagent for detecting the TOMM34 mRNA may be immobilized on a solid matrix. Moreover, more than one reagent for detecting the TOMM34 mRNA may be included in the kit.

On the other hand, examples of reagents suitable for detecting the TOMM34 protein or the immunologically fragment thereof may include antibodies to the TOMM34 protein or the immunologically fragment thereof. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the TOMM34 protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the TOMM34 protein may be included in the kit.

The kit may contain more than one of the aforementioned reagents. The kit can further include a solid matrix and reagent for binding a probe against a TOMM34 gene or antibody against a TOMM34 peptide, a medium and container for culturing cells, positive and negative control reagents, and a secondary antibody for detecting an antibody against a TOMM34 peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

In one embodiment of the present invention, when the reagent is a probe against the TOMM34 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of TOMM34 mRNA present in the sample. The detection sites may be configured in any suitably detectable shape and are typically in the shape of a bar or dot spanning the width of a test strip.

The kit of the present invention may further include a positive control sample or TOMM34 standard sample. The positive control sample of the present invention may be prepared by collecting TOMM34 positive samples and then assaying their TOMM34 levels. Alternatively, a purified TOMM34 protein or polynucleotide may be added to cells that do not express TOMM34 to form the positive sample or the TOMM34 standard sample. In the present invention, purified TOMM34 may be a recombinant protein. The TOMM34 level of the positive control sample is, for example, more than the cut off value.

In one embodiment, the present invention further provides a diagnostic kit including, a protein or a partial protein thereof specifically recognized by the antibody of the present invention or the fragment thereof.

Examples of the partial peptide of the protein of the present invention include polypeptides consisting of at least 8, preferably 15, and more preferably 20 contiguous amino acids in the amino acid sequence of the protein of the present invention. Cancer can be diagnosed by detecting an antibody in a sample (e.g., blood, tissue) using a protein or a peptide (polypeptide) of the present invention. The method for preparing the protein of the present invention and peptides are as described above.

The present invention provides methods for diagnosing cancer, which can be performed by determining the difference between the amount of anti-TOMM34 antibody and that in the corresponding control sample as describe above. The subject is suspected to be suffering from cancer, if cells or tissues of the subject contain antibodies against the expression products (TOMM34) of the gene and the quantity of the anti-TOMM34 antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides a method or diagnostic agents for evaluating immunological response of subject by using peptide epitopes as described herein. In one embodiment of the invention, HLA A-2 restricted peptides as described herein are used as reagents for evaluating or predicting an immune response of a subject. The immune response to be evaluated is induced by contacting an immunogen with immunocompetent cells in vitro or in vivo. In preferred embodiments, the immunocompetent cells for evaluating an immunological response, may be selected among peripheral blood, peripheral blood lymphocyte (PBL), and peripheral blood mononuclear cell (PBMC). Methods for collecting or isolating such immunocompetent cells are well known in the arts. In some embodiments, any agent that may result in the production of antigen specific CTLs that recognize and bind to the peptide epitope (s) may be employed as the reagent. The peptide reagent need not be used as the immunogen. Assay systems that are used for such an analysis include relatively recent technical developments such as tetramers, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as follows:
A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen-specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et aL, J. Clin. Invest. 100: 503-513, 1997 and Penna et aL, J Exp. Med. 174: 1565-1570, 1991) comprising peptides of the present invention. For example, patient PBMC samples from individuals with cancer to be treated are analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may be also used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in that patient are selected for the analysis. The immunogenicity of the vaccine may be indicated by the presence of epitope-specific CTLs in the PBMC sample.

The peptides of the invention may be also used to make antibodies, using techniques well known in the art (see, e.g. CURRENTPROTOCOLSINIMMUNOLOGY, Wiley/Greene, NY; and Antibodies A Laboratory Manual, Harlow and Lane, Cold Spring Harbor Laboratory Press, 1989), which may be useful as reagents to diagnose or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a TOMM34 immunogenic polypeptide. These methods include the step of determining expression level of the peptide of the present invention, or a complex of the peptide of the present invention and an HLA class I molecule in a biological sample. The expression of a peptide or complex of peptide and HLA class I molecule can be determined or detected by assaying with a binding partner for the peptide or complex. In an preferred embodiment, a binding partner for the peptide or complex is an antibody recognizes and specifically bind to the peptide. The expression of TOMM34 in a biological sample, such as a tumor biopsy, can also be tested by standard PCR amplification protocols using TOMM34 primers. An example of tumor expression is presented herein and further disclosure of exemplary conditions and primers for TOMM34 amplification can be found in WO2003/27322.

Preferably, the diagnostic methods include the step of contacting a biological sample isolated from a subject with an agent specific for the peptide of the present invention to detect the presence of the peptide of the present invention in the biological sample. As used herein, "contacting" means placing the biological sample in sufficient proximity to the agent and under the appropriate conditions of, e.g., concentration, temperature, time, ionic strength, to allow the specific interaction between the agent and the peptide of the present invention that are present in the biological sample.

In general, the conditions for contacting the agent with the biological sample are conditions known by those of ordinary skill in the art to facilitate a specific interaction between a molecule and its cognate (e.g., a protein and its receptor, an antibody and its protein antigen, a nucleic acid and its complementary strand) in a biological sample. Optimal conditions for facilitating a specific interaction between a molecule and its cognate are described in U.S. Pat. No. 5,108,921, issued to Low et al.

The diagnostic method of the present invention can be performed in either or both of in vivo and in vitro. Accordingly, biological sample can be located in vivo or in vitro in the present invention. For example, the biological sample can be a tissue in vivo and the agent specific for the TOMM34 immunogenic polypeptide can be used to detect the presence of such molecules in the tissue. Alternatively, the biological sample can be collected or isolated in vitro (e.g., a blood sample, tumor biopsy specimen, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labelled HLA multimeric complexes (for example, Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Tetramer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

For instance, in some embodiments, the present invention provides a method for diagnosing or evaluating an immunological response of a subject administered at least one of TOMM34 peptides of the present invention, the method including the steps of:

(a) contacting an immunogen with immunocompetent cells under the condition suitable
of induction of CTL specific to the immunogen;

(b) detecting or determining induction level of the CTL induced in step (a); and (c) correlating the immunological response of the subject with the CTL induction level.

In the present invention, the immunogen preferably includes at least one of (a) TOMM34 peptide(s) of the present invention, for example, peptides having the amino acid sequence selected from among SEQ ID NOs: 1, 5, 31 and 32, and modified peptides thereof (peptides having such amino acid sequences, and peptides having in which such amino acid sequences have been modified with 1, 2 or more amino acid substitution(s)). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction. In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol. According to the present invention, enhanced induction of immunogen specific CTL as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any TOMM34 peptides. (e.g. random amino acid sequence). In a preferred embodiment, the immunological response of the subject is evaluated in a sequence specific manner, by comparison with an immunological response between each immunogen administered to the subject. In particular, even when a mixture of some kinds of TOMM34 peptides is administered to the subject, immunological response might vary depending on the peptides. In that case, by comparison of the immunological response between each peptide, peptides to which the subject show higher response can be identified.

XI. ANTIBODIES

The present invention provides antibodies that bind to the peptide of the present invention. Preferred antibodies specifically bind to the peptide of the present invention and will not bind (or will bind weakly) to non-peptide of the present invention. Alternatively, antibodies bind the peptide of the invention as well as the homologs thereof.

Antibodies against the peptide of the invention can find use in cancer diagnostic and prognostic assays, and imaging methodologies. Similarly, such antibodies can find use in the treatment, diagnosis, and/or prognosis of other cancers, to the extent TOMM34 is also expressed or over-expressed in cancer patient. Moreover, intracellularly expressed antibodies (e.g., single chain antibodies) are therapeutically useful in treating cancers in which the expression of TOMM34 is involved, examples of which include, but are not limited to AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

The present invention also provides various immunological assay for the detection and/or quantification of the TOMM34 protein (SEQ ID NO: 42) or fragments thereof including the peptides of the present invention. Such assays can comprise one or more anti-TOMM34 antibodies capable of recognizing and binding a TOMM34 protein or fragments thereof, as appropriate. In the context of the present invention, anti-TOMM34 antibodies binding to TOMM34 polypeptide preferably recognize a peptide of the present invention. A binding specificity of antibody can be confirmed with inhibition test. That is, when the binding between an antibody to be analyzed and full-length of TOMM34 polypeptide was inhibited under presence of a peptide of the present invention, it is shown that this antibody specifically binds to the fragment. In the context of the present invention, such immunological assays are performed within various immunological assay formats well known in the art, including but not limited to various types of radioimmunoassays, immuno-chromatograph technique, enzyme-linked immunosorbent assays (ELISA), enzyme-linked immunofluorescent assays (ELIFA), and the like.

Related immunological but non-antibody assays of the invention also comprise T cell immunogenicity assays (inhibitory or stimulatory) as well as major histocompatibility complex (MHC) binding assays. In addition, immunological imaging methods capable of detecting cancers expressing TOMM34 are also provided by the invention, including but not limited to radioscintigraphic imaging methods using labeled antibodies of the present invention. Such assays are clinically useful in the detection, monitoring, and prognosis of TOMM34 expressing cancers, examples of which include, but are not limited to, AML, CML, bladder cancer, breast cancer, cervical cancer, colorectal cancer, esophagus cancer, liver cancer, osteosarcoma, prostate cancer, renal carcinoma, SCLC, NSCLC and soft tissue tumor.

The present invention provides antibodies that bind to the peptide of the invention. An antibody of the invention can be used in any form, such as monoclonal or polyclonal antibodies, and includes antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may comprise, for example, the amino (N)-terminal or carboxy (C)-terminal fragment of a peptide of the present invention.

Herein, an antibody of the present invention is defined as a protein that reacts with either the full length or a fragment of a TOMM34 peptide. In a preferred embodiment, an antibody of the present invention recognizes fragment peptides of TOMM34 having an amino acid sequence selected from among SEQ ID NOs: 1, 5, 31 and 32. Methods for synthesizing oligopeptide are well known in the arts. After the synthesis, peptides may be optionally purified prior to use as immunogen. In the present invention, the oligopeptide (e.g. 9 or 10 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or its fragment may be inserted into a known expression vector, which is then used to transform a host cell as described herein. The desired peptide or its fragment may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primates are used. Animals of Rodentia include, for example, mouse, rat and hamster. Animals of Lagomorpha include, for example, rabbit. Animals of Primates include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')2, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, J. Mol. Biol. 227:381 (1991), Similarly, human antibodies can be made by introducing a human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Examples of suitable chromatography methods, with the exception of affinity includes, for example, ion-exchange chromatography, hydrophobic chromatography, gel filtration, reverse-phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a peptide of the invention, by exposing an antibody of the invention to a sample presumed to contain a peptide of the invention, and detecting or measuring the immune complex formed by the antibody and the peptide.

Because the method of detection or measurement of the peptide according to the invention can specifically detect or measure a peptide, the method may be useful in a variety of experiments in which the peptide is used.

XII. VECTORS AND HOST CELLS

The present invention also provides a vector and host cell into which a nucleotide encoding the peptide of the present invention is introduced. A vector of the present invention is useful to keep a nucleotide, especially a DNA, of the present invention in host cell, to express the peptide of the present invention, or to administer the nucleotide of the present invention for gene therapy.

When *E. coli* is a host cell and the vector is amplified and produced in a large amount in *E. coli* (e.g., JM109, DH5 alpha, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT and pT7 can also be used for subcloning and extracting cDNA as well as the vectors described above. When a vector is used to produce the protein of the present invention, an expression vector is especially useful. For example, an expression vector to be expressed in *E. coli* should have the above characteristics to be amplified in *E. coli*. When *E. coli*, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Although methods and materials similar or equivalent to those described herein can be used in the practice or testing of the present invention, suitable methods and materials are described. All publications, patent applications, patents, and other references mentioned herein are incorporated by reference in their entirety. In case of conflict, the present specification, including definitions, will control. In addition, the materials, methods, and examples are illustrative only and not intended to be limiting.

The following examples are presented to illustrate the present invention and to assist one of ordinary skill in making and using the same. The examples are not intended in any way to otherwise limit the scope of the present invention.

EXAMPLES

Materials and Methods

Cell Lines

T2, HLA-A*0201-positive B-lymphoblastoid cell line, and COS7, African green monkey kidney cell line, were purchased from ATCC.

Candidate Selection of Peptides Derived from TOMM34

9-mer and 10-mer peptides derived from TOMM34 that bind to HLA-A*0201 molecule were predicted using binding prediction software "BIMAS" (http://www-bimas.cit.nih.gov/molbio/hla_bind) (Parker et al. (J Immunol 1994, 152(1): 163-75), Kuzushima et al. (Blood 2001, 98(6): 1872-81)). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide at 20 mg/ml and stored at −80 degrees C.

In Vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells isolated from a normal volunteer (HLA-A*0201 positive) by Ficoll-Paque plus (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X ray-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 TU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, IFN-gamma ELISPOT assay and IFN-gamma ELISA were performed. Peptide-pulsed T2 ($1 \times 10^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and HLA-A02

The cDNA encoding an open reading frame of target genes or HLA-A*0201 was amplified by PCR. The PCR-amplified product was cloned into expression vector. The plasmids were transfected into COS7, which is the target genes and HLA-A*0201-null cell line, using lipofectamine 2000 (Invitrogen) according to the manufacturer's recommended procedures. After 2 days from transfection, the transfected cells were harvested with versene (Invitrogen) and used as the stimulator cells ($5 \times 10^4$ cells/well) for CTL activity assay.

Results 1

Enhanced TOMM34 Expression in Cancers

The wide gene expression profile data obtained from various cancers using cDNA-microarray revealed that TOMM34 (GenBank Accession No. NM_006809; for example, SEQ ID No: 42) expression was elevated. TOMM34 expression was validly elevated in 4 out of 28 AMLs, 4 out of 14 CMLs, 8 out of 11 bladder cancers, 1 out of 4 breast cancers, 1 out of 5 cervical cancers, 12 out of 12 colorectal cancers, 5 out of 17 esophagus cancers, 6 out of 6 liver cancers, 1 out of 10 osteosarcoma, 1 out of 26 prostate cancers, 1 out of 19 renal carcinomas, 2 out of 14 SCLCs, 5 out of 20 NSCLCs and 10 out of 51 soft tissue tumors as compared with corresponding normal tissues (Table 1).

TABLE 1

Ratio of cases observed up-regulation of TOMM34 in cancerous tissue as compared with normal corresponding tissue

| Cancer | Ratio |
|---|---|
| AML | 4/28 |
| CML | 4/14 |
| Bladder Cancer | 8/11 |
| Breast Cancer | 1/4 |
| Cervical Cancer | 1/5 |
| Colorectal Cancer | 12/12 |
| Esophagus Cancer | 5/17 |
| Liver Cancer | 6/6 |
| Osteosarcoma | 1/10 |
| Prostate Cancer | 1/26 |
| Renal Carcinoma | 1/19 |
| SCLC | 2/14 |
| NSCLC | 5/20 |
| Soft Tissue Tumor | 10/51 |

Results 2

Prediction of HLA-A02 Binding Peptides Derived from TOMM34

Table 2a and 2b show the HLA-A02 binding 9mer and 10mer peptides of TOMM34 in the order of high binding affinity. A total of 40 peptides with potential HLA-A02 binding ability were selected and examined to determine the epitope peptides.

TABLE 2a

HLA-A02 binding 9mer peptides derived from TOMM34

| Start Position | amino acid sequence | score | SEQ ID NO |
|---|---|---|---|
| 30 | ALYGRALRV | 222.566 | 1 |
| 77 | ALALVPFSI | 60.51 | 2 |
| 52 | VLYSNRAAC | 27.026 | 3 |
| 110 | TVLQIDDNV | 11.034 | 4 |
| 220 | LLCSNLESA | 9.518 | 5 |
| 230 | YSNRALCYL | 8.115 | 6 |
| 103 | MAYVDYKTV | 7.883 | 7 |
| 80 | LVPFSIKPL | 7.309 | 8 |
| 255 | KLDGKNVKA | 6.955 | 9 |
| 23 | GQYAEASAL | 6.931 | 10 |
| 195 | VLKEEGNEL | 5.211 | 11 |
| 111 | VLQIDDNVT | 5.194 | 12 |
| 238 | LVLKQYTEA | 4.101 | 13 |
| 1 | MAPKFPDSV | 3.058 | 14 |
| 113 | QIDDNVTSA | 2.577 | 15 |
| 253 | ALKLDGKN | 2.434 | 16 |
| 239 | VLKQYTEAV | 2.028 | 17 |

TABLE 2a-continued

HLA-A02 binding 9mer peptides derived from TOMM34

| Start Position | amino acid sequence | score | SEQ ID NO |
|---|---|---|---|
| 144 | LPSIPLVPV | 1.775 | 18 |
| 142 | LKLPSIPLV | 1.398 | 19 |
| 279 | SSFADISNL | 1.187 | 20 |

TABLE 2b

HLA-A02 binding 10mer peptides derived from TOMM34

| Start Position | amino acid sequence | score | SEQ ID NO |
|---|---|---|---|
| 143 | KLPSiPLVPV | 559.894 | 21 |
| 97 | ALEKyPMAYV | 56.309 | 22 |
| 79 | ALVPfSIKPL | 49.134 | 23 |
| 237 | YLVLkQYTEA | 34.279 | 24 |
| 135 | SLGPeWRLKL | 21.362 | 25 |
| 219 | SLLCsNLESA | 20.716 | 26 |
| 238 | LVLKqYTEAV | 18.757 | 27 |
| 127 | RMTRaLMDSL | 17.388 | 28 |
| 113 | QIDDnVTSAV | 15.684 | 29 |
| 241 | KQYTeAVKDC | 12.975 | 30 |
| 30 | ALYGrALRVL | 12.893 | 31 |
| 220 | LLCSnLESAT | 12.668 | 32 |
| 195 | VLKEeGNELV | 8.314 | 33 |
| 112 | LQIDdNVTSA | 8.075 | 34 |
| 194 | RVLKeEGNEL | 6.916 | 35 |
| 299 | KLRQeVKQNL | 5.682 | 36 |
| 141 | RLKLpSIPLV | 5.599 | 37 |
| 160 | SLPSeNHKEM | 4.968 | 38 |
| 175 | KETTaTKNRV | 4.733 | 39 |
| 186 | SAGDvEKARV | 3.961 | 40 |

Start position indicates the number of amino acid residue from the N-terminus of TOMM34.

Binding score is derived from "BIMAS".

CTL Induction with the Predicted Peptides from TOMM34 Restricted with HLA-A*0201

CTLs for those peptides derived from TOMM34 were generated according to the protocols as described in "Materials and Methods". Peptide specific CTL activity was detected by IFN-gamma ELISPOT assay (FIG. 1a-d). The following well numbers demonstrated potent IFN-gamma production as compared to the control wells: well number #4 with TOMM34-A02-9-30 (SEQ ID NO: 1) (a), #2 with TOMM34-A02-9-220 (SEQ ID NO: 5) (b), #4 with TOMM34-A02-10-30 (SEQ ID NO: 31) (c) and #2 with TOMM34-A02-10-220 (SEQ ID NO: 32) (d). On the other hand, no specific CTL activity was detected by stimulation with other peptides shown in Table 2a and 2b, despite those peptides had possible binding activity with HLA-A*0201. As a typical case of negative data, specific IFN-gamma production was not observed from the CTL stimulated with TOMM34-A02-10-143 (SEQ ID NO: 21) (e). As a result, it indicated that 4 peptides derived from TOMM34 were selected as the peptides that could induce potent CTLs.

Establishment of CTL Line and Clone Against TOMM34 Derived Peptide

Figure 2:
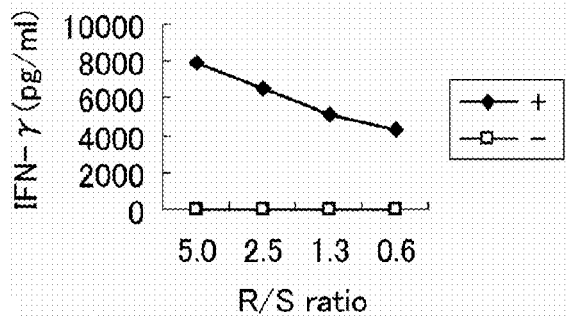
FIG. 2 is a line graph depicting the IFN-gamma production of the CTL line stimulated with TOMM34-A02-9-30 (SEQ ID NO: 1). The quantity of IFN-gamma which CTL produced was measured by IFN-gamma enzyme-linked immunosorbent assay (ELISA). The results demonstrate that CTL line established by stimulation with this peptide show potent TN-gamma production as compared with the control. In the figures, "+" indicates the IFN-gamma production against target cells pulsed with the appropriate peptide, and "−" indicates the IFN-gamma production against target cells not pulsed with any peptides.
Figure 3:
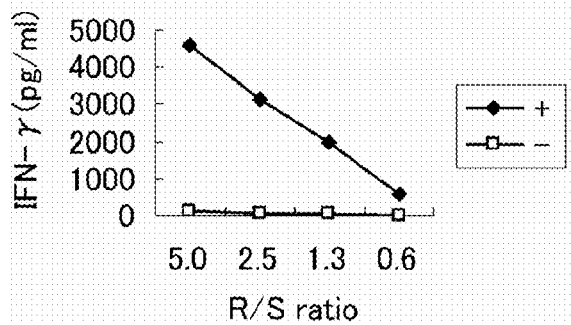
FIG. 3 is a line graph depicting the IFN-gamma production of the CTL clone established by limiting dilution from the CTL line stimulated with TOMM34-A02-9-30 (SEQ ID NO:1). The results demonstrate that the CTL clone established by stimulation with this peptide show potent IFN-gamma production as compared with the control. In the figure, "+" indicates the IFN-gamma production against target cells pulsed with the appropriate peptide and "−" indicates the IFN-gamma production against target cells not pulsed with any peptides.

The cells that showed peptide specific CTL activity detected by IFN-gamma ELISPOT assay in the well number #4 with TOMM34-A02-9-30 (SEQ ID NO: 1) was expanded and CTL line was established by expansion procedure as described in the "Materials and Methods" section above. CTL activity of this CTL line was measured by IFN-gamma ELISA assay (FIG. 2). The CTL line demonstrated potent IFN-gamma production against the target cells pulsed with the corresponding peptide as compared to target cells without peptide pulse. Furthermore, the CTL clone was established by limiting dilution from the CTL line as described in "Materials and Methods", and IFN-gamma production from the CTL clone against target cells pulsed peptide was measured by IFN-gamma ELISA assay. Potent IFN-gamma production was observed from the CTL clone stimulated with TOMM34-A02-9-30 (SEQ ID NO: 1) (FIG. 3).

Specific CTL Activity Against Target Cells Expressing TOMM34 and HLA-A*0201

Figure 4:
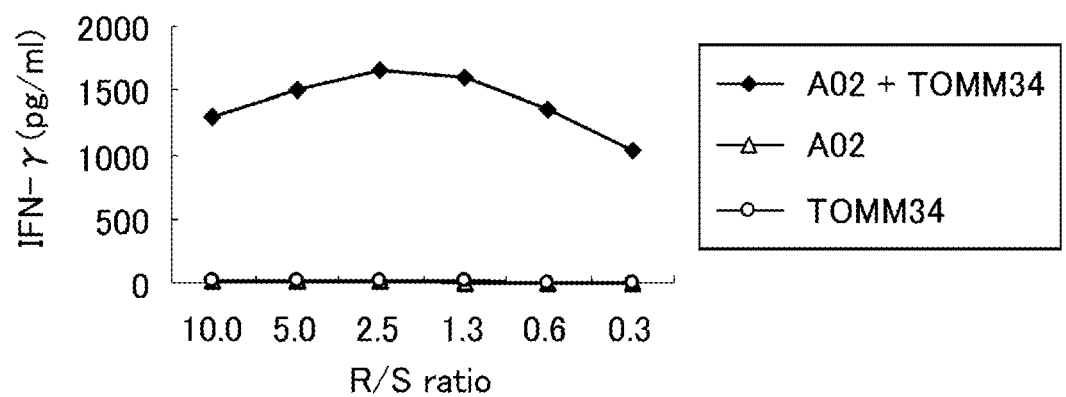
FIG. 4 is a line graph depicting the specific CTL activity against target cells that express TOMM34 and HLA-A*0201. COS7 cells transfected with HLA-A'0201 or the full length TOMM34 gene were prepared as the controls. The CTL line established with TOMM34-A02-9-30 (SEQ TD NO:1) showed specific CTL activity against COS7 cells transfected with both TOMM34 and HLA-A*0201 (black lozenge). On the other hand, no significant specific CTL activity was detected against target cells expressing either HLA-A*0201 (triangle) or TOMM34 (circle).

The established CTL line raised against TOMM34-A02-9-30 (SEQ ID NO: 1) peptide was examined for the ability to recognize target cells that express TOMM34 and HLA-A*0201 molecule. COS7 cells transfected with both the full length of TOMM34 and HLA-A*0201 gene (a specific model for the target cells that express TOMM34 and HLA-A*0201 gene) were prepared as stimulator cells, and COS7 cells transfected with either full length of TOMM34 or HLA-A*0201 were used as the controls. In FIG. 4, the CTL line stimulated with TOMM34-A02-9-30 (SEQ ID NO: 1) showed potent CTL activity against COS7 cells expressing both TOMM34 and HLA-A*0201. On the other hand, no significant specific CTL activity was detected against the controls. Thus, these data clearly demonstrated that TOMM34-A02-9-30 (SEQ ID NO: 1) peptide was endogenously processed and presented on the target cells with HLA-A*0201 molecule and was recognized by the CTLs. These results indicate that this peptide derived from TOMM34 may be suitable as a cancer vaccine for patients with TOMM34 expressing tumors.

Homology Analysis of Antigen Peptides

The CTLs stimulated with TOMM34-A02-9-30 (SEQ ID NO: 1), TOMM34-A02-9-220 (SEQ ID NO: 5), TOMM34-A02-10-30 (SEQ ID NO: 31) and TOMM34-A02-10-220 (SEQ ID NO: 32) showed significant and specific CTL activity. This result may be due to the fact that the sequence of TOMM34-A02-9-30 (SEQ ID NO: 1), TOMM34-A02-9-220 (SEQ ID NO: 5), TOMM34-A02-10-30 (SEQ ID NO: 31) and TOMM34-A02-10-220 (SEQ ID NO: 32) are homologous to peptide derived from other molecules that are known to sensitize the human immune system. To exclude this possibility, homology analyses were performed for these peptide sequences using as queries the BLAST algorithm (http://www.ncbi.nlm.nih.gov/blast/blast.cgi) which revealed no sequence with significant homology. The results of homology analyses indicate that the sequence of TOMM34-A02-9-30 (SEQ ID NO: 1), TOMM34-A02-9-220 (SEQ ID NO: 5), TOMM34-A02-10-30 (SEQ ID NO: 31) and TOMM34-A02-10-220 (SEQ ID NO: 32) are unique and thus, there is little possibility, to our best knowledge, that this molecules raise unintended immunologic response to some unrelated molecule. In conclusion, we identified novel HLA-A*0201 epitope peptides derived from TOMM34. Furthermore, the results herein demonstrate that epitope peptide of TOMM34 may be suitable for use in cancer immunotherapy.

INDUSTRIAL APPLICABILITY

The present invention provides new TAAs, particularly those derived from TOMM34 that induce potent and specific anti-tumor immune responses and have applicability to a wide array of cancer types. Such TAAs are useful as peptide vaccines against diseases associated with TOMM34, e.g., cancer, more particularly, AML, CML, bladder cancer, breast cancer, cervical cancer, colorectal cancer, esophagus cancer, liver cancer, osteosarcoma, prostate cancer, renal carcinoma, SCLC, NSCLC and, soft tissue tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. A method for inducing an antigen-presenting cell (APC) with CTL inducibility, wherein the method comprises a step selected from the group consisting of:
   (a) collecting APCs from a subject, and
   (b) contacting an APC with a peptide in vitro, ex vivo or in vivo
   wherein the peptide is selected from the group consisting of:
   an isolated peptide of less than 15 amino acids comprising an amino acid sequence as shown in SEQ ID NO: 5, and
   an isolated peptide of less than 15 amino acids comprising an amino acid sequence in which one or two amino acid(s) are substituted, deleted, inserted or added to an amino acid sequence as shown in SEQ ID NO: 5 to yield a modified peptide that retains the ability to bind to an HLA antigen and cytotoxic T lymphocyte (CTL) inducibility.

2. A method for inducing a CTL, comprising a step selected from the group consisting of:
   (a) co-culturing a CD8-positive T cell with an APC that presents on its surface a complex of an HLA antigen and a peptide, and
   (b) co-culturing a CD8-positive T cell with an exosome that presents on its surface a complex of an HLA antigen and the peptide
   wherein the peptide is selected from the group consisting of:
   an isolated peptide of less than 15 amino acids comprising an amino acid sequence as shown in SEQ ID NO: 5, and
   an isolated peptide of less than 15 amino acids comprising an amino acid sequence in which one or two amino acid(s) are substituted, deleted, inserted or added to an amino acid sequence as shown in SEQ ID NO: 5 to yield a modified peptide that retains the ability to bind to an HLA antigen and cytotoxic T lymphocyte (CTL) inducibility.

3. A method of inducing an immune response against cancer in a subject, wherein the method comprises a step of administering to the subject a peptide, or an immunologically active fragment thereof, wherein the peptide is selected from the group consisting of:
   an isolated peptide of less than 15 amino acids comprising an amino acid sequence as shown in SEQ ID NO: 5, and
   an isolated peptide of less than 15 amino acids comprising an amino acid sequence in which one or two amino acid(s) are substituted, deleted, inserted or added to an amino acid sequence as shown in SEQ ID NO: 5 to yield a modified peptide that retains the ability to bind to an HLA antigen and cytotoxic T lymphocyte (CTL) inducibility.

4. The method of claim 1, wherein the peptide consists of the amino acid sequence of SEQ ID NO: 5.

5. The method of claim 1, wherein the peptide has one or both of the following characteristics:
   (a) the second amino acid from the N-terminus of the amino acid sequence of SEQ ID NO: 5 is substituted with methionine; and
   (b) the C-terminal amino acid of the amino acid sequence of SEQ ID NO: 5 is substituted with valine or leucine.

6. The method of claim 2, wherein the peptide consists of the amino acid sequence of SEQ ID NO: 5.

7. The method of claim 2, wherein the peptide has one or both of the following characteristics:
   (a) the second amino acid from the N-terminus of the amino acid sequence of SEQ ID NO: 5 is substituted with methionine; and
   (b) the C-terminal amino acid of the amino acid sequence of SEQ ID NO: 5 is substituted with valine or leucine.

8. The method of claim 3, wherein the peptide consists of the amino acid sequence of SEQ ID NO: 5.

9. The method of claim 3, wherein the peptide has one or both of the following characteristics:
- (a) the second amino acid from the N-terminus of the amino acid sequence of SEQ ID NO: 5 is substituted with methionine; and
- (b) the C-terminal amino acid of the amino acid sequence of SEQ ID NO: 5 is substituted with valine or leucine.

* * * * *